(12) United States Patent
Darby et al.

(10) Patent No.: US 8,637,455 B2
(45) Date of Patent: Jan. 28, 2014

(54) COMPOSITIONS AND METHODS FOR DELIVERY OF GLYCOPEPTIDE ANTIBIOTICS TO MEDICAL DEVICE SURFACES

(75) Inventors: Martyn K. Darby, Chapel Hill, NC (US); Isaac G. Sanford, Durham, NC (US); R. Edward Benson, Durham, NC (US); Hanne Gron, Durham, NC (US); Paul T. Hamilton, Cary, NC (US); Shrikumar A. Nair, Cary, NC (US); Doug Buechter, Chester Springs, PA (US); Elliott Gruskin, Malvern, PA (US)

(73) Assignees: Affinergy, LLC, RTP, NC (US); DePuy Synthes Products, LLC, Raynham, MA (US)

( * ) Notice: Subject to any disclaimer, the term of this patent is extended or adjusted under 35 U.S.C. 154(b) by 578 days.

(21) Appl. No.: 12/739,353

(22) PCT Filed: Oct. 17, 2008

(86) PCT No.: PCT/US2008/080321
§ 371 (c)(1),
(2), (4) Date: Jul. 28, 2010

(87) PCT Pub. No.: WO2009/055313
PCT Pub. Date: Apr. 30, 2009

(65) Prior Publication Data
US 2011/0038912 A1 Feb. 17, 2011

Related U.S. Application Data

(60) Provisional application No. 60/981,565, filed on Oct. 22, 2007, provisional application No. 61/056,746, filed on May 28, 2008.

(51) Int. Cl.
*A61K 38/04* (2006.01)
*A01N 37/18* (2006.01)

(52) U.S. Cl.
USPC .......................................................... 514/3.1

(58) Field of Classification Search
None
See application file for complete search history.

(56) References Cited

U.S. PATENT DOCUMENTS

| 5,520,664 | A | 5/1996 | Bricault, Jr. et al. |
| 5,624,704 | A | 4/1997 | Darouiche et al. |
| 5,709,672 | A | 1/1998 | Illner |
| 5,902,283 | A | 5/1999 | Darouiche et al. |
| 6,083,913 | A * | 7/2000 | Dower et al. .................. 514/7.8 |
| 6,261,271 | B1 | 7/2001 | Solomon et al. |
| 6,361,526 | B1 | 3/2002 | Reisdorf et al. |
| 7,192,717 | B2 | 3/2007 | Hill et al. |
| 7,208,011 | B2 | 4/2007 | Shanley et al. |
| 7,238,669 | B2 | 7/2007 | Bishop-Hurley et al. |
| 2006/0123505 | A1 | 6/2006 | Kikuchi et al. |
| 2007/0104758 | A1 | 5/2007 | Hamilton et al. |
| 2007/0160644 | A1 | 7/2007 | Kenan et al. |

FOREIGN PATENT DOCUMENTS

| EP | 1793875 B1 | 9/2006 |
| WO | WO 2006/098744 | 9/2006 |
| WO | WO-2009054967 A2 | 4/2009 |

OTHER PUBLICATIONS

European Patent Application No. 08843011.1: Extended European Search Report dated Dec. 9, 2011, 7 pages.
Cooper, et al., "Binding of Vancomycin Group Antibiotics to D-Alanine and D-Lactate Presenting Self-Assembled Monolayers," Bioorganic & Medicinal Chemistry 2000, 2609-2616, 8, XP-002664326.
Rao, et al., "Binding of a Dimeric Derivative of Vancomycin to L-Lys-D-Ala-D-Lactate in Solution and at a Surface," Chemistry & Biology, May 18, 1999, 6, 6, 353-359, XP-26904687.
"International Application Serial No. PCT/US2008/012011, International Search Report mailed Oct. 2, 2009", 5 pgs.
"International Application Serial No. PCT/US2008/012011, Written Opinion mailed Oct. 2, 2009", 8 pgs.
"International Application Serial No. PCT/US2008/080321, International Search Report mailed Mar. 17, 2009", 4 pgs.
Nagarajan, R., "Antibacterial Activities and Modes of Action of Vancomycin and Related Glycopeptides", *Antimicrobial Agents and Chemotherapy*, 35(4), (1991), 605-609.
Rios, R., et al., "Differential resopnse to exogenous and endogenous myostatin in myoblasts suggests that myostatin acts as an autocrine factor in vivo", *Endocrinology*, 145(6), (2004), 2795-2803.

* cited by examiner

*Primary Examiner* — Thomas Heard
(74) *Attorney, Agent, or Firm* — Woodcock Washburn LLP

(57) ABSTRACT

The presently disclosed subject matter relates to peptides having binding affinity for glycopeptide antibiotics and methods and compositions for delivering glycopeptide antibiotic to the surface of medical devices. The peptide compositions can comprise a peptide having binding affinity for a surface material of a medical device that is coupled to the peptide having binding affinity for glycopeptide antibiotic. Also provided are methods of applying the peptide compositions to a medical device by contacting the peptide compositions with a surface of the medical device. In addition, kits are provided comprising the peptide compositions.

14 Claims, No Drawings

SEQUENCE LISTING

```
<160> NUMBER OF SEQ ID NOS: 131

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide

<400> SEQUENCE: 1

Cys Leu Ile Asp Met Tyr Gly Val Cys His Asn Phe Asp Gly Ala Tyr
1               5                   10                  15

Asp Ser

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Cys Leu Phe Asp Ile Phe Gly Val Cys His Ser Phe Asp Gly Ala Tyr
1               5                   10                  15

Asp Ser

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Pro Cys Glu Leu Ile Asp Met Phe Gly Asn Asp His Cys Pro
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Synthetic peptide

<400> SEQUENCE: 4

Ser Cys Asp Met Leu Phe Cys Glu Asn Phe Ser Gly Ser Gly Asn Asn
1               5                   10                  15

Trp Phe Ser

<210> SEQ ID NO 5
<211> LENGTH: 18
<212> TYPE: PRT
<213> ORGANISM: Artificial Sequence
```

```
<220> FEATURE:
<223> OTHER INFORMATION: Synthetic peptide

<400> SEQUENCE: 5

Ser Leu Ile Asp Met Tyr Gly Val Cys His Asn Phe Asp Gly Ala Tyr
1               5                   10                  15

Asp Ser

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(12)
<223> OTHER INFORMATION: Cysteine residues 1 and 12 are disulfide bonded
<220> FEATURE:
<221> NAME/KEY: MISC_FEATURE
<222> LOCATION: (2)..(4)
<223> OTHER INFORMATION: Residues 2, 3 and 4 can be present or absent
<220> FEATURE:
<221> NAME/KEY: MISC_FEATURE
<222> LOCATION: (9)..(11)
<223> OTHER INFORMATION: Residues 9, 10 and 11 can be present or absent

<400> SEQUENCE: 6

Cys Xaa Xaa Xaa Asp Met Phe Gly Xaa Xaa Xaa Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Either Xaa1 or Xaa2 is C and Xaa2 can be absent
      if Xaa1 is C
<220> FEATURE:
<221> NAME/KEY: MISC_FEATURE
<222> LOCATION: (3)..(3)
<223> OTHER INFORMATION: Position three is L, M, I, V or A
<220> FEATURE:
<221> NAME/KEY: MISC_FEATURE
<222> LOCATION: (4)..(4)
<223> OTHER INFORMATION: Position four is I, M or F
<220> FEATURE:
<221> NAME/KEY: MISC_FEATURE
<222> LOCATION: (5)..(5)
<223> OTHER INFORMATION: Position five is D or C
<220> FEATURE:
<221> NAME/KEY: MISC_FEATURE
<222> LOCATION: (6)..(6)
<223> OTHER INFORMATION: Position six is M or I
<220> FEATURE:
<221> NAME/KEY: MISC_FEATURE
<222> LOCATION: (7)..(7)
<223> OTHER INFORMATION: Position seven is F or Y
<220> FEATURE:
<221> NAME/KEY: MISC_FEATURE
<222> LOCATION: (8)..(8)
<223> OTHER INFORMATION: Position eight is G
<220> FEATURE:
<221> NAME/KEY: MISC_FEATURE
<222> LOCATION: (9)..(9)
<223> OTHER INFORMATION: Position nine is any amino acid except C or P
<220> FEATURE:
<221> NAME/KEY: MISC_FEATURE
<222> LOCATION: (10)..(10)
<223> OTHER INFORMATION: If position 11 or 12 is C, position 10 is any
      amino acid except C and can be absent
```

```
<220> FEATURE:
<221> NAME/KEY: MISC_FEATURE
<222> LOCATION: (11)..(11)
<223> OTHER INFORMATION: Position 11 is C or H unless position 10 or 12
      is C and then position 11 is not C
<220> FEATURE:
<221> NAME/KEY: MISC_FEATURE
<222> LOCATION: (12)..(12)
<223> OTHER INFORMATION: Position 12 is C or H unless position 10 or 11
      is C and then position 12 is not C

<400> SEQUENCE: 7

Xaa Xaa Xaa Xaa Xaa Xaa Xaa Xaa Xaa Xaa Xaa Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Either Xaa1 or Xaa2 is C and Xaa2 can be absent
      if Xaa1 is C
<220> FEATURE:
<221> NAME/KEY: MISC_FEATURE
<222> LOCATION: (3)..(3)
<223> OTHER INFORMATION: Position 3 is not C, G, P, Q or T
<220> FEATURE:
<221> NAME/KEY: MISC_FEATURE
<222> LOCATION: (4)..(4)
<223> OTHER INFORMATION: Position 4 is not A, G, P or S
<220> FEATURE:
<221> NAME/KEY: MISC_FEATURE
<222> LOCATION: (5)..(5)
<223> OTHER INFORMATION: Position 5 is D or C
<220> FEATURE:
<221> NAME/KEY: MISC_FEATURE
<222> LOCATION: (6)..(6)
<223> OTHER INFORMATION: Position 6 is M or I
<220> FEATURE:
<221> NAME/KEY: MISC_FEATURE
<222> LOCATION: (7)..(7)
<223> OTHER INFORMATION: Position 7 is F or Y
<220> FEATURE:
<221> NAME/KEY: MISC_FEATURE
<222> LOCATION: (8)..(8)
<223> OTHER INFORMATION: Position 8 is not A, R, S or V
<220> FEATURE:
<221> NAME/KEY: MISC_FEATURE
<222> LOCATION: (9)..(9)
<223> OTHER INFORMATION: Position 9 is not C or P
<220> FEATURE:
<221> NAME/KEY: MISC_FEATURE
<222> LOCATION: (10)..(10)
<223> OTHER INFORMATION: If position 11 or 12 is C, position 10 is any
      amino acid except C and can be absent
<220> FEATURE:
<221> NAME/KEY: MISC_FEATURE
<222> LOCATION: (11)..(11)
<223> OTHER INFORMATION: Position 11 is C or H unless position 10 or 12
      is C and then position 11 is not C
<220> FEATURE:
<221> NAME/KEY: MISC_FEATURE
<222> LOCATION: (12)..(12)
<223> OTHER INFORMATION: Position 12 is C or H unless position 10 or 11
      is C and then position 12 is not C

<400> SEQUENCE: 8

Xaa Xaa Xaa Xaa Xaa Xaa Xaa Xaa Xaa Xaa Xaa Xaa
1               5                   10

<210> SEQ ID NO 9
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 9

Ser Thr Cys Leu Ile Asp Met Tyr Gly Val Cys His
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Synthetic peptide

<400> SEQUENCE: 10

Ser Thr Cys Leu Ile Asp Met Tyr Gly Val Cys His Ser Ser Cys Leu
1               5                   10                  15

Ile Asp Met Tyr Gly Val Cys His
            20

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Ser Thr Cys Leu Ile Ala Met Tyr Gly Val Cys His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Ser Thr Cys Leu Ile Glu Met Tyr Gly Val Cys His
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Ser Thr Cys Leu Ile Asp Met Tyr Ser Val Cys His
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide

<400> SEQUENCE: 14

Phe Leu Ser Phe Val Phe Pro Ala Ser Ala Trp Gly Gly
1               5                   10

<210> SEQ ID NO 15
```

```
<211> LENGTH: 13
<212> TYPE: PRT
<213> ORGANISM: Artificial Sequence
<220> FEATURE:
<223> OTHER INFORMATION: Synthetic peptide

<400> SEQUENCE: 15

Phe Tyr Met Pro Phe Gly Pro Thr Trp Trp Gln His Val
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Leu Phe Ser Trp Phe Leu Pro Thr Asp Asn Tyr Pro Val
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Phe Met Asp Ile Trp Ser Pro Trp His Leu Leu Gly Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Phe Ser Ser Leu Phe Phe Pro His Trp Pro Ala Gln Leu
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Synthetic peptide

<400> SEQUENCE: 19

Ser Cys Ala Met Ala Gln Trp Phe Cys Asp Arg Ala Glu Pro His His
1               5                   10                  15

Val Ile Ser

<210> SEQ ID NO 20
<211> LENGTH: 19
<212> TYPE: PRT
<213> ORGANISM: Artificial Sequence
<220> FEATURE:
<223> OTHER INFORMATION: Synthetic peptide

<400> SEQUENCE: 20

Ser Cys Asn Met Ser His Leu Thr Gly Val Ser Leu Cys Asp Ser Leu
1               5                   10                  15

Ala Thr Ser
```

```
<210> SEQ ID NO 21
<211> LENGTH: 19
<212> TYPE: PRT
<213> ORGANISM: Artificial Sequence
<220> FEATURE:
<223> OTHER INFORMATION: Synthetic peptide

<400> SEQUENCE: 21

Ser Cys Val Tyr Ser Phe Ile Asp Gly Ser Gly Cys Asn Ser His Ser
1               5                   10                  15

Leu Gly Ser

<210> SEQ ID NO 22
<211> LENGTH: 19
<212> TYPE: PRT
<213> ORGANISM: Artificial Sequence
<220> FEATURE:
<223> OTHER INFORMATION: Synthetic peptide

<400> SEQUENCE: 22

Ser Cys Ser Gly Phe His Leu Leu Cys Glu Ser Arg Ser Met Gln Arg
1               5                   10                  15

Glu Leu Ser

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide

<400> SEQUENCE: 23

Ser Cys Gly Ile Leu Cys Ser Ala Phe Pro Phe Asn Asn His Gln Val
1               5                   10                  15

Gly Ala Ser

<210> SEQ ID NO 24
<211> LENGTH: 19
<212> TYPE: PRT
<213> ORGANISM: Artificial Sequence
<220> FEATURE:
<223> OTHER INFORMATION: Synthetic peptide

<400> SEQUENCE: 24

Ser Cys Cys Ser Met Phe Phe Lys Asn Val Ser Tyr Val Gly Ala Ser
1               5                   10                  15

Asn Pro Ser

<210> SEQ ID NO 25
<211> LENGTH: 19
<212> TYPE: PRT
<213> ORGANISM: Artificial Sequence
<220> FEATURE:
<223> OTHER INFORMATION: Synthetic peptide

<400> SEQUENCE: 25

Ser Cys Pro Ile Trp Lys Tyr Cys Asp Asp Tyr Ser Arg Ser Gly Ser
1               5                   10                  15

Ile Phe Ser

<210> SEQ ID NO 26
<211> LENGTH: 18
<212> TYPE: PRT
<213> ORGANISM: Artificial Sequence
```

```
<220> FEATURE:
<223> OTHER INFORMATION: Synthetic peptide

<400> SEQUENCE: 26

Ser Cys Leu Phe Asn Ser Met Lys Cys Leu Val Leu Ile Leu Cys Phe
1               5                   10                  15

Val Ser

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Ser Cys Tyr Val Asn Gly His Asn Ser Val Trp Val Val Phe Trp
1               5                   10                  15

Gly Val Ser

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide

<400> SEQUENCE: 28

Ser Cys Asp Phe Val Cys Asn Val Leu Phe Asn Val Asn His Gly Ser
1               5                   10                  15

Asn Met Ser

<210> SEQ ID NO 29
<211> LENGTH: 19
<212> TYPE: PRT
<213> ORGANISM: Artificial Sequence
<220> FEATURE:
<223> OTHER INFORMATION: Synthetic peptide

<400> SEQUENCE: 29

Ser Cys Leu Asn Lys Phe Phe Val Leu Met Ser Val Gly Leu Arg Ser
1               5                   10                  15

Tyr Thr Ser

<210> SEQ ID NO 30
<211> LENGTH: 19
<212> TYPE: PRT
<213> ORGANISM: Artificial Sequence
<220> FEATURE:
<223> OTHER INFORMATION: Synthetic peptide

<400> SEQUENCE: 30

Ser Cys Cys Asn His Asn Ser Thr Ser Val Lys Asp Val Gln Phe Pro
1               5                   10                  15

Thr Leu Ser

<210> SEQ ID NO 31
<211> LENGTH: 13
<212> TYPE: PRT
<213> ORGANISM: Artificial Sequence
<220> FEATURE:
<223> OTHER INFORMATION: Synthetic peptide

<400> SEQUENCE: 31
```

Phe Phe Pro Ser Ser Trp Tyr Ser His Leu Gly Val Leu
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic peptide

<400> SEQUENCE: 32

Phe Phe Gly Phe Asp Val Tyr Asp Met Ser Asn Ala Leu
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic peptide

<400> SEQUENCE: 33

Leu Ser Phe Ser Asp Phe Tyr Phe Ser Glu Gly Ser Glu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic peptide

<400> SEQUENCE: 34

Phe Ser Tyr Ser Val Ser Tyr Ala His Pro Glu Gly Leu
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic peptide

<400> SEQUENCE: 35

Leu Pro His Leu Ile Gln Tyr Arg Val Leu Leu Val Ser
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Synthetic peptide

<400> SEQUENCE: 36

Ser Cys Tyr Val Asn Gly His Asn Ser Val Trp Val Val Phe Trp
1               5                   10                  15

Gly Val Ser

<210> SEQ ID NO 37
<211> LENGTH: 19
<212> TYPE: PRT
<213> ORGANISM: Artificial Sequence
<220> FEATURE:
<223> OTHER INFORMATION: Synthetic peptide

<400> SEQUENCE: 37

-continued

Ser Cys Asn Ser Phe Met Phe Ile Asn Gly Ser Phe Lys Glu Thr Gly
1               5                   10                  15

Gly Cys Ser

<210> SEQ ID NO 38
<211> LENGTH: 19
<212> TYPE: PRT
<213> ORGANISM: Artificial Sequence
<220> FEATURE:
<223> OTHER INFORMATION: Synthetic peptide

<400> SEQUENCE: 38

Ser Cys Phe Gly Asn Leu Gly Asn Leu Ile Tyr Thr Cys Asp Arg Leu
1               5                   10                  15

Met Pro Ser

<210> SEQ ID NO 39
<211> LENGTH: 19
<212> TYPE: PRT
<213> ORGANISM: Artificial Sequence
<220> FEATURE:
<223> OTHER INFORMATION: Synthetic peptide

<400> SEQUENCE: 39

Ser Cys Ser Phe Phe Met Pro Trp Cys Asn Phe Leu Asn Gly Glu Met
1               5                   10                  15

Ala Val Ser

<210> SEQ ID NO 40
<211> LENGTH: 19
<212> TYPE: PRT
<213> ORGANISM: Artificial Sequence
<220> FEATURE:
<223> OTHER INFORMATION: Synthetic peptide

<400> SEQUENCE: 40

Ser Cys Phe Gly Asn Val Phe Cys Val Tyr Asn Gln Phe Ala Ala Gly
1               5                   10                  15

Leu Phe Ser

<210> SEQ ID NO 41
<211> LENGTH: 19
<212> TYPE: PRT
<213> ORGANISM: Artificial Sequence
<220> FEATURE:
<223> OTHER INFORMATION: Synthetic peptide

<400> SEQUENCE: 41

Ser Cys Cys Phe Ile Asn Ser Asn Phe Ser Val Met Asn His Ser Leu
1               5                   10                  15

Phe Lys Ser

<210> SEQ ID NO 42
<211> LENGTH: 19
<212> TYPE: PRT
<213> ORGANISM: Artificial Sequence
<220> FEATURE:
<223> OTHER INFORMATION: Synthetic peptide

<400> SEQUENCE: 42

Ser Cys Asp Tyr Phe Ser Phe Leu Glu Cys Phe Ser Asn Gly Trp Ser
1               5                   10                  15

Gly Ala Ser

```
<210> SEQ ID NO 43
<211> LENGTH: 19
<212> TYPE: PRT
<213> ORGANISM: Artificial Sequence
<220> FEATURE:
<223> OTHER INFORMATION: Synthetic peptide

<400> SEQUENCE: 43

Ser Cys Trp Met Gly Leu Phe Glu Cys Pro Asp Ala Trp Leu His Asp
1               5                   10                  15

Trp Asp Ser

<210> SEQ ID NO 44
<211> LENGTH: 19
<212> TYPE: PRT
<213> ORGANISM: Artificial Sequence
<220> FEATURE:
<223> OTHER INFORMATION: Synthetic peptide

<400> SEQUENCE: 44

Ser Cys Phe Trp Tyr Ser Trp Leu Cys Ser Ala Ser Ser Ser Asp Ala
1               5                   10                  15

Leu Ile Ser

<210> SEQ ID NO 45
<211> LENGTH: 19
<212> TYPE: PRT
<213> ORGANISM: Artificial Sequence
<220> FEATURE:
<223> OTHER INFORMATION: Synthetic peptide

<400> SEQUENCE: 45

Ser Cys Phe Gly Asn Phe Leu Ser Phe Gly Phe Asn Cys Glu Ser Ala
1               5                   10                  15

Leu Gly Ser

<210> SEQ ID NO 46
<211> LENGTH: 19
<212> TYPE: PRT
<213> ORGANISM: Artificial Sequence
<220> FEATURE:
<223> OTHER INFORMATION: Synthetic peptide

<400> SEQUENCE: 46

Ser Cys Leu Tyr Cys His Leu Asn Asn Gln Phe Leu Ser Trp Val Ser
1               5                   10                  15

Gly Asn Ser

<210> SEQ ID NO 47
<211> LENGTH: 19
<212> TYPE: PRT
<213> ORGANISM: Artificial Sequence
<220> FEATURE:
<223> OTHER INFORMATION: Synthetic peptide

<400> SEQUENCE: 47

Ser Cys Phe Gly Phe Ser Asp Cys Leu Ser Trp Phe Val Gln Pro Ser
1               5                   10                  15

Thr Ala Ser

<210> SEQ ID NO 48
<211> LENGTH: 19
<212> TYPE: PRT
<213> ORGANISM: Artificial Sequence
```

```
<220> FEATURE:
<223> OTHER INFORMATION: Synthetic peptide

<400> SEQUENCE: 48

Ser Cys Asn His Leu Gly Phe Phe Ser Phe Cys Asp Arg Leu Val
1               5                   10                  15

Glu Asn Ser

<210> SEQ ID NO 49
<211> LENGTH: 19
<212> TYPE: PRT
<213> ORGANISM: Artificial Sequence
<220> FEATURE:
<223> OTHER INFORMATION: Synthetic peptide

<400> SEQUENCE: 49

Ser Cys Gly Tyr Phe Cys Ser Phe Tyr Asn Tyr Leu Asp Ile Gly Thr
1               5                   10                  15

Ala Ser Ser

<210> SEQ ID NO 50
<211> LENGTH: 19
<212> TYPE: PRT
<213> ORGANISM: Artificial Sequence
<220> FEATURE:
<223> OTHER INFORMATION: Synthetic peptide

<400> SEQUENCE: 50

Ser Cys Asn Ser Ser Tyr Ser Trp Tyr Cys Trp Phe Gly Gly Ser
1               5                   10                  15

Ser Pro Ser

<210> SEQ ID NO 51
<211> LENGTH: 13
<212> TYPE: PRT
<213> ORGANISM: Artificial Sequence
<220> FEATURE:
<223> OTHER INFORMATION: Synthetic peptide

<400> SEQUENCE: 51

Phe Gly His Gly Trp Leu Asn Thr Leu Asn Leu Gly Trp
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic peptide

<400> SEQUENCE: 52

Phe Ser Pro Phe Ser Ala Asn Leu Trp Tyr Asp Met Phe
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic peptide

<400> SEQUENCE: 53

Val Phe Val Pro Phe Gly Asn Trp Leu Ser Thr Ser Val
1               5                   10
```

```
<210> SEQ ID NO 54
<211> LENGTH: 13
<212> TYPE: PRT
<213> ORGANISM: Artificial Sequence
<220> FEATURE:
<223> OTHER INFORMATION: Synthetic peptide

<400> SEQUENCE: 54

Phe Trp Asn Val Asn Tyr Asn Pro Trp Gly Trp Asn Tyr
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic peptide

<400> SEQUENCE: 55

Phe Tyr Trp Asp Arg Leu Asn Val Gly Trp Gly Leu Leu
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic peptide

<400> SEQUENCE: 56

Leu Tyr Ser Thr Met Tyr Pro Gly Met Ser Trp Leu Val
1               5                   10

<210> SEQ ID NO 57
<211> LENGTH: 19
<212> TYPE: PRT
<213> ORGANISM: Artificial Sequence
<220> FEATURE:
<223> OTHER INFORMATION: Synthetic peptide

<400> SEQUENCE: 57

Ser Cys Phe Tyr Gln Asn Val Ile Ser Ser Phe Ala Gly Asn Pro
1               5                   10                  15

Trp Glu Cys

<210> SEQ ID NO 58
<211> LENGTH: 19
<212> TYPE: PRT
<213> ORGANISM: Artificial Sequence
<220> FEATURE:
<223> OTHER INFORMATION: Synthetic peptide

<400> SEQUENCE: 58

Ser Cys Asn Met Leu Leu Asn Ser Leu Pro Leu Pro Ser Glu Asp Trp
1               5                   10                  15

Ser Ala Cys

<210> SEQ ID NO 59
<211> LENGTH: 19
<212> TYPE: PRT
<213> ORGANISM: Artificial Sequence
<220> FEATURE:
<223> OTHER INFORMATION: Synthetic peptide

<400> SEQUENCE: 59

Ser Cys Pro Phe Thr His Ser Leu Ala Leu Asn Thr Asp Arg Ala Ser
1               5                   10                  15
```

Pro Gly Cys

<210> SEQ ID NO 60
<211> LENGTH: 19
<212> TYPE: PRT
<213> ORGANISM: Artificial Sequence
<220> FEATURE:
<223> OTHER INFORMATION: Synthetic peptide

<400> SEQUENCE: 60

Ser Cys Phe Glu Ser Asp Phe Pro Asn Val Arg His His Val Leu Lys
1               5                   10                  15

Gln Ser Cys

<210> SEQ ID NO 61
<211> LENGTH: 19
<212> TYPE: PRT
<213> ORGANISM: Artificial Sequence
<220> FEATURE:
<223> OTHER INFORMATION: Synthetic peptide

<400> SEQUENCE: 61

Ser Cys Val Phe Asp Ser Lys His Phe Ser Pro Thr His Ser Pro His
1               5                   10                  15

Asp Val Cys

<210> SEQ ID NO 62
<211> LENGTH: 19
<212> TYPE: PRT
<213> ORGANISM: Artificial Sequence
<220> FEATURE:
<223> OTHER INFORMATION: Synthetic peptide

<400> SEQUENCE: 62

Ser Cys Gly Asp His Met Thr Asp Lys Asn Met Pro Asn Ser Gly Ile
1               5                   10                  15

Ser Gly Cys

<210> SEQ ID NO 63
<211> LENGTH: 19
<212> TYPE: PRT
<213> ORGANISM: Artificial Sequence
<220> FEATURE:
<223> OTHER INFORMATION: Synthetic peptide

<400> SEQUENCE: 63

Ser Cys Asp Phe Phe Asn Arg His Gly Tyr Asn Ser Gly Cys Glu His
1               5                   10                  15

Ser Val Cys

<210> SEQ ID NO 64
<211> LENGTH: 19
<212> TYPE: PRT
<213> ORGANISM: Artificial Sequence
<220> FEATURE:
<223> OTHER INFORMATION: Synthetic peptide

<400> SEQUENCE: 64

Ser Cys Gly Asp His Met Thr Asp Lys Asn Met Pro Asn Ser Gly Ile
1               5                   10                  15

Ser Gly Cys

<210> SEQ ID NO 65

```
<211> LENGTH: 19
<212> TYPE: PRT
<213> ORGANISM: Artificial Sequence
<220> FEATURE:
<223> OTHER INFORMATION: Synthetic peptide

<400> SEQUENCE: 65

Ser Cys Tyr Tyr Asn Gly Leu Val Val His His Ser Asn Ser Gly His
1               5                   10                  15

Lys Asp Cys

<210> SEQ ID NO 66
<211> LENGTH: 18
<212> TYPE: PRT
<213> ORGANISM: Artificial Sequence
<220> FEATURE:
<223> OTHER INFORMATION: Synthetic peptide

<400> SEQUENCE: 66

Cys Trp Ser Arg Phe Arg Leu Phe Met Leu Phe Cys Met Phe Tyr Leu
1               5                   10                  15

Val Ser

<210> SEQ ID NO 67
<211> LENGTH: 18
<212> TYPE: PRT
<213> ORGANISM: Artificial Sequence
<220> FEATURE:
<223> OTHER INFORMATION: Synthetic peptide

<400> SEQUENCE: 67

Cys Ile Lys Tyr Pro Phe Leu Tyr Cys Cys Leu Leu Ser Leu Phe Leu
1               5                   10                  15

Phe Ser

<210> SEQ ID NO 68
<211> LENGTH: 16
<212> TYPE: PRT
<213> ORGANISM: Artificial Sequence
<220> FEATURE:
<223> OTHER INFORMATION: Synthetic peptide

<400> SEQUENCE: 68

Ser Trp Trp Gly Phe Trp Asn Gly Ser Ala Ala Pro Val Trp Ser Arg
1               5                   10                  15

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Ser Trp Asp Phe Arg Ser Leu Arg Asp Trp Trp Pro Pro Ala Pro Ser
1               5                   10                  15

Leu Ser Ser Arg
            20

<210> SEQ ID NO 70
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 70

Ser Ile Phe Ser Thr Trp Asn Pro Trp Ser Pro Tyr Ser Val Ser Arg
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide

<400> SEQUENCE: 71

Ser Phe Gly Ser Trp Trp Trp Gly Ser Gly Ala Ala Ser Ser Arg
1               5                   10                  15

<210> SEQ ID NO 72
<211> LENGTH: 19
<212> TYPE: PRT
<213> ORGANISM: Artificial Sequence
<220> FEATURE:
<223> OTHER INFORMATION: Synthetic peptide

<400> SEQUENCE: 72

Ser Cys Phe Trp Phe Leu Arg Trp Ser Leu Phe Ile Val Leu Phe Thr
1               5                   10                  15

Cys Cys Ser

<210> SEQ ID NO 73
<211> LENGTH: 19
<212> TYPE: PRT
<213> ORGANISM: Artificial Sequence
<220> FEATURE:
<223> OTHER INFORMATION: Synthetic peptide

<400> SEQUENCE: 73

Ser Cys Glu Ser Val Asp Cys Phe Ala Asp Ser Arg Met Ala Lys Val
1               5                   10                  15

Ser Met Ser

<210> SEQ ID NO 74
<211> LENGTH: 19
<212> TYPE: PRT
<213> ORGANISM: Artificial Sequence
<220> FEATURE:
<223> OTHER INFORMATION: Synthetic peptide

<400> SEQUENCE: 74

Ser Cys Val Gly Phe Phe Cys Ile Thr Gly Ser Asp Val Ala Ser Val
1               5                   10                  15

Asn Ser Ser

<210> SEQ ID NO 75
<211> LENGTH: 19
<212> TYPE: PRT
<213> ORGANISM: Artificial Sequence
<220> FEATURE:
<223> OTHER INFORMATION: Synthetic peptide

<400> SEQUENCE: 75

Ser Cys Ser Asp Cys Leu Lys Ser Val Asp Phe Ile Pro Ser Ser Leu
1               5                   10                  15

Ala Ser Ser

<210> SEQ ID NO 76
```

```
<211> LENGTH: 19
<212> TYPE: PRT
<213> ORGANISM: Artificial Sequence
<220> FEATURE:
<223> OTHER INFORMATION: Synthetic peptide

<400> SEQUENCE: 76

Ser Cys Ala Phe Asp Cys Pro Ser Ser Val Ala Arg Ser Pro Gly Glu
1               5                   10                  15

Trp Ser Ser

<210> SEQ ID NO 77
<211> LENGTH: 18
<212> TYPE: PRT
<213> ORGANISM: Artificial Sequence
<220> FEATURE:
<223> OTHER INFORMATION: Synthetic peptide

<400> SEQUENCE: 77

Ser Cys Val Asp Val Met His Ala Asp Ser Pro Gly Pro Asp Gly Leu
1               5                   10                  15

Asn Ser

<210> SEQ ID NO 78
<211> LENGTH: 19
<212> TYPE: PRT
<213> ORGANISM: Artificial Sequence
<220> FEATURE:
<223> OTHER INFORMATION: Synthetic peptide

<400> SEQUENCE: 78

Ser Cys Ser Ser Phe Glu Val Ser Glu Met Phe Thr Cys Ala Val Ser
1               5                   10                  15

Ser Tyr Ser

<210> SEQ ID NO 79
<211> LENGTH: 19
<212> TYPE: PRT
<213> ORGANISM: Artificial Sequence
<220> FEATURE:
<223> OTHER INFORMATION: Synthetic peptide

<400> SEQUENCE: 79

Ser Cys Gly Leu Asn Phe Pro Leu Cys Ser Phe Val Asp Phe Ala Gln
1               5                   10                  15

Asp Ala Ser

<210> SEQ ID NO 80
<211> LENGTH: 19
<212> TYPE: PRT
<213> ORGANISM: Artificial Sequence
<220> FEATURE:
<223> OTHER INFORMATION: Synthetic peptide

<400> SEQUENCE: 80

Ser Cys Met Leu Phe Ser Ser Val Phe Asp Cys Gly Met Leu Ile Ser
1               5                   10                  15

Asp Leu Ser

<210> SEQ ID NO 81
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 81

Ser Cys Val Asp Tyr Val Met His Ala Asp Ser Pro Gly Pro Asp Gly
1               5                   10                  15

Leu Asn Ser

<210> SEQ ID NO 82
<211> LENGTH: 19
<212> TYPE: PRT
<213> ORGANISM: Artificial Sequence
<220> FEATURE:
<223> OTHER INFORMATION: Synthetic peptide

<400> SEQUENCE: 82

Ser Cys Ser Glu Asn Phe Met Phe Asn Met Tyr Gly Thr Gly Val Cys
1               5                   10                  15

Thr Glu Ser

<210> SEQ ID NO 83
<211> LENGTH: 13
<212> TYPE: PRT
<213> ORGANISM: Artificial Sequence
<220> FEATURE:
<223> OTHER INFORMATION: Synthetic peptide

<400> SEQUENCE: 83

His Lys His Pro Val Thr Pro Arg Phe Phe Val Val Glu
1               5                   10

<210> SEQ ID NO 84
<211> LENGTH: 18
<212> TYPE: PRT
<213> ORGANISM: Artificial Sequence
<220> FEATURE:
<223> OTHER INFORMATION: Synthetic peptide

<400> SEQUENCE: 84

Cys Asn Cys Tyr Val Thr Pro Asn Leu Leu Lys His Lys Cys Tyr Lys
1               5                   10                  15

Ile Cys

<210> SEQ ID NO 85
<211> LENGTH: 18
<212> TYPE: PRT
<213> ORGANISM: Artificial Sequence
<220> FEATURE:
<223> OTHER INFORMATION: Synthetic peptide

<400> SEQUENCE: 85

Cys Ser His Asn His His Lys Leu Thr Ala Lys His Gln Val Ala His
1               5                   10                  15

Lys Cys

<210> SEQ ID NO 86
<211> LENGTH: 18
<212> TYPE: PRT
<213> ORGANISM: Artificial Sequence
<220> FEATURE:
<223> OTHER INFORMATION: Synthetic peptide

<400> SEQUENCE: 86

Cys Asp Gln Asn Asp Ile Phe Tyr Thr Ser Lys Lys Ser His Lys Ser
1               5                   10                  15

His Cys
```

<210> SEQ ID NO 87
<211> LENGTH: 18
<212> TYPE: PRT
<213> ORGANISM: Artificial Sequence
<220> FEATURE:
<223> OTHER INFORMATION: Synthetic peptide

<400> SEQUENCE: 87

Ser Ser Asp Val Tyr Leu Val Ser His Lys His His Leu Thr Arg His
1               5                   10                  15

Asn Ser

<210> SEQ ID NO 88
<211> LENGTH: 18
<212> TYPE: PRT
<213> ORGANISM: Artificial Sequence
<220> FEATURE:
<223> OTHER INFORMATION: Synthetic peptide

<400> SEQUENCE: 88

Ser Asp Lys Cys His Lys His Trp Tyr Cys Tyr Glu Ser Lys Tyr Gly
1               5                   10                  15

Gly Ser

<210> SEQ ID NO 89
<211> LENGTH: 18
<212> TYPE: PRT
<213> ORGANISM: Artificial Sequence
<220> FEATURE:
<223> OTHER INFORMATION: Synthetic peptide

<400> SEQUENCE: 89

Ser Asp Lys Ser His Lys His Trp Tyr Ser Tyr Glu Ser Lys Tyr Gly
1               5                   10                  15

Gly Ser

<210> SEQ ID NO 90
<211> LENGTH: 14
<212> TYPE: PRT
<213> ORGANISM: Artificial Sequence
<220> FEATURE:
<223> OTHER INFORMATION: Synthetic peptide

<400> SEQUENCE: 90

His His Lys Leu Lys His Gln Met Leu His Leu Asn Gly Gly
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic peptide

<400> SEQUENCE: 91

Gly His His His Lys Lys Asp Gln Leu Pro Gln Leu Gly Gly
1               5                   10

<210> SEQ ID NO 92
<211> LENGTH: 17
<212> TYPE: PRT
<213> ORGANISM: Artificial Sequence
<220> FEATURE:
<223> OTHER INFORMATION: Synthetic peptide

```
<400> SEQUENCE: 92

Ser Ser His Lys His Pro Val Thr Pro Arg Phe Phe Val Val Glu Ser
1               5                   10                  15

Arg

<210> SEQ ID NO 93
<211> LENGTH: 22
<212> TYPE: PRT
<213> ORGANISM: Artificial Sequence
<220> FEATURE:
<223> OTHER INFORMATION: Synthetic peptide

<400> SEQUENCE: 93

Ser Ser Cys Asn Cys Tyr Val Thr Pro Asn Leu Leu Lys His Lys Cys
1               5                   10                  15

Tyr Lys Ile Cys Ser Arg
            20

<210> SEQ ID NO 94
<211> LENGTH: 22
<212> TYPE: PRT
<213> ORGANISM: Artificial Sequence
<220> FEATURE:
<223> OTHER INFORMATION: Synthetic peptide

<400> SEQUENCE: 94

Ser Ser Cys Ser His Asn His His Lys Leu Thr Ala Lys His Gln Val
1               5                   10                  15

Ala His Lys Cys Ser Arg
            20

<210> SEQ ID NO 95
<211> LENGTH: 22
<212> TYPE: PRT
<213> ORGANISM: Artificial Sequence
<220> FEATURE:
<223> OTHER INFORMATION: Synthetic peptide

<400> SEQUENCE: 95

Ser Ser Cys Asp Gln Asn Asp Ile Phe Tyr Thr Ser Lys Lys Ser His
1               5                   10                  15

Lys Ser His Cys Ser Arg
            20

<210> SEQ ID NO 96
<211> LENGTH: 22
<212> TYPE: PRT
<213> ORGANISM: Artificial Sequence
<220> FEATURE:
<223> OTHER INFORMATION: Synthetic peptide

<400> SEQUENCE: 96

Ser Ser Ser Ser Asp Val Tyr Leu Val Ser His Lys His His Leu Thr
1               5                   10                  15

Arg His Asn Ser Ser Arg
            20

<210> SEQ ID NO 97
<211> LENGTH: 22
<212> TYPE: PRT
<213> ORGANISM: Artificial Sequence
<220> FEATURE:
<223> OTHER INFORMATION: Synthetic peptide

<400> SEQUENCE: 97
```

```
Ser Ser Ser Asp Lys Cys His Lys His Trp Tyr Cys Tyr Glu Ser Lys
1               5                   10                  15

Tyr Gly Gly Ser Ser Arg
            20
```

<210> SEQ ID NO 98
<211> LENGTH: 14
<212> TYPE: PRT
<213> ORGANISM: Artificial Sequence
<220> FEATURE:
<223> OTHER INFORMATION: Synthetic peptide

<400> SEQUENCE: 98

```
His His Lys Leu Lys His Gln Met Leu His Leu Asn Gly Gly
1               5                   10
```

<210> SEQ ID NO 99
<211> LENGTH: 14
<212> TYPE: PRT
<213> ORGANISM: Artificial Sequence
<220> FEATURE:
<223> OTHER INFORMATION: Synthetic peptide

<400> SEQUENCE: 99

```
Gly His His His Lys Lys Asp Gln Leu Pro Gln Leu Gly Gly
1               5                   10
```

<210> SEQ ID NO 100
<211> LENGTH: 13
<212> TYPE: PRT
<213> ORGANISM: Artificial Sequence
<220> FEATURE:
<223> OTHER INFORMATION: Synthetic peptide

<400> SEQUENCE: 100

```
Cys Phe Val Leu Asn Cys His Leu Val Leu Asp Arg Pro
1               5                   10
```

<210> SEQ ID NO 101
<211> LENGTH: 19
<212> TYPE: PRT
<213> ORGANISM: Artificial Sequence
<220> FEATURE:
<223> OTHER INFORMATION: Synthetic peptide

<400> SEQUENCE: 101

```
Ser Cys Phe Gly Asn Phe Leu Ser Phe Gly Phe Asn Cys Glu Tyr Ala
1               5                   10                  15

Leu Gly Ser
```

<210> SEQ ID NO 102
<211> LENGTH: 13
<212> TYPE: PRT
<213> ORGANISM: Artificial Sequence
<220> FEATURE:
<223> OTHER INFORMATION: Synthetic peptide

<400> SEQUENCE: 102

```
Asp Gly Phe Phe Ile Leu Tyr Lys Asn Pro Asp Val Leu
1               5                   10
```

<210> SEQ ID NO 103
<211> LENGTH: 7
<212> TYPE: PRT
<213> ORGANISM: Artificial Sequence
<220> FEATURE:

<223> OTHER INFORMATION: Synthetic peptide

<400> SEQUENCE: 103

Asn His Gln Asn Gln Thr Asn
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Ala Thr His Met Val Gly Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Gly Ile Asn Pro Asn Phe Ile
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Thr Ala Ile Ser Gly His Phe
1               5

<210> SEQ ID NO 107
<211> LENGTH: 13
<212> TYPE: PRT
<213> ORGANISM: Artificial Sequence
<220> FEATURE:
<223> OTHER INFORMATION: Synthetic peptide

<400> SEQUENCE: 107

Leu Tyr Gly Thr Pro Glu Tyr Ala Val Gln Pro Leu Arg
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic peptide

<400> SEQUENCE: 108

Cys Phe Leu Thr Gln Asp Tyr Cys Val Leu Ala Gly Lys
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic peptide

```
-continued

<400> SEQUENCE: 109

Val Leu His Leu Asp Ser Tyr Gly Pro Ser Val Pro Leu
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic peptide

<400> SEQUENCE: 110

Val Val Asp Ser Thr Gly Tyr Leu Arg Pro Val Ser Thr
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic peptide

<400> SEQUENCE: 111

Val Leu Gln Asn Ala Thr Asn Val Ala Pro Phe Val Thr
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic peptide

<400> SEQUENCE: 112

Trp Trp Ser Ser Met Pro Tyr Val Gly Asp Tyr Thr Ser
1               5                   10

<210> SEQ ID NO 113
<211> LENGTH: 19
<212> TYPE: PRT
<213> ORGANISM: Artificial Sequence
<220> FEATURE:
<223> OTHER INFORMATION: Synthetic peptide

<400> SEQUENCE: 113

Ser Ser Tyr Phe Asn Leu Gly Leu Val Lys His Asn His Val Arg His
1               5                   10                  15

His Asp Ser

<210> SEQ ID NO 114
<211> LENGTH: 18
<212> TYPE: PRT
<213> ORGANISM: Artificial Sequence
<220> FEATURE:
<223> OTHER INFORMATION: Synthetic peptide

<400> SEQUENCE: 114

Cys His Asp His Ser Asn Lys Tyr Leu Lys Ser Trp Lys His Gln Gln
1               5                   10                  15

Asn Cys

<210> SEQ ID NO 115
<211> LENGTH: 19
<212> TYPE: PRT
<213> ORGANISM: Artificial Sequence
<220> FEATURE:
```

<223> OTHER INFORMATION: Synthetic peptide

<400> SEQUENCE: 115

Ser Cys Lys His Asp Ser Glu Phe Ile Lys Lys His Val His Ala Val
1               5                   10                  15

Lys Lys Cys

<210> SEQ ID NO 116
<211> LENGTH: 19
<212> TYPE: PRT
<213> ORGANISM: Artificial Sequence
<220> FEATURE:
<223> OTHER INFORMATION: Synthetic peptide

<400> SEQUENCE: 116

Ser Cys His His Leu Lys His Asn Thr His Lys Glu Ser Lys Met His
1               5                   10                  15

His Glu Cys

<210> SEQ ID NO 117
<211> LENGTH: 11
<212> TYPE: PRT
<213> ORGANISM: Artificial Sequence
<220> FEATURE:
<223> OTHER INFORMATION: Synthetic peptide

<400> SEQUENCE: 117

Val Asn Lys Met Asn Arg Leu Trp Glu Pro Leu
1               5                   10

<210> SEQ ID NO 118
<211> LENGTH: 19
<212> TYPE: PRT
<213> ORGANISM: Artificial Sequence
<220> FEATURE:
<223> OTHER INFORMATION: Synthetic peptide

<400> SEQUENCE: 118

Ser Ser His Arg Thr Asn His Lys Lys Asn Asn Pro Lys Lys Lys Asn
1               5                   10                  15

Lys Thr Arg

<210> SEQ ID NO 119
<211> LENGTH: 19
<212> TYPE: PRT
<213> ORGANISM: Artificial Sequence
<220> FEATURE:
<223> OTHER INFORMATION: Synthetic peptide

<400> SEQUENCE: 119

Asn His Thr Ile Ser Lys Asn His Lys Lys Lys Asn Lys Asn Ser Asn
1               5                   10                  15

Lys Thr Arg

<210> SEQ ID NO 120
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (25)..(25)
<223> OTHER INFORMATION: Residue 25 is a linker comprised of 2 PEG
      [poly(ethylene) glycol] units having the shortest ether structure
      possible of PEG with two ethylene oxide unitsas follows:

-continued (HN-CH2-CH2-O-CH2-CH2-O-CH2-C=O)2

<400> SEQUENCE: 120

Ser Ser Ser Cys Leu Ile Asp Met Tyr Gly Val Cys His Asn Phe Asp
1               5                   10                  15

Gly Ala Tyr Asp Ser Ser Arg Gly Xaa Ser Ser His Arg Thr Asn His
            20                  25                  30

Lys Lys Asn Asn Pro Lys Lys Lys Asn Lys Thr Arg Gly Ser Ser Gly
        35                  40                  45

Lys

<210> SEQ ID NO 121
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 121
tgtttgattg atatgtatgg tgtttgccat aattttgatg gggcgtatga tagc        54

<210> SEQ ID NO 122
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 122
tgtctgtttg atattttggg tgtttgtcac agctttgatg gggcgtatga tagc        54

<210> SEQ ID NO 123
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 123
ccgtgtgagc tgattgatat gtttgggaat gatcattgtc cg                    42

<210> SEQ ID NO 124
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 4 residues of aminoundecanoic acid ("AUD") are
      added sequentially to the N-terminus during linear synthesis
<220> FEATURE:
<221> NAME/KEY: MISC_FEATURE
<222> LOCATION: (25)..(25)
<223> OTHER INFORMATION: Residue 25 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 124

Ser Ser Ser Cys Leu Ile Asp Met Tyr Gly Val Cys His Asn Phe Asp
1               5                   10                  15

Gly Ala Tyr Asp Ser Ser Arg Gly Xaa Ser Ser His Arg Thr Asn His
            20                  25                  30

Lys Lys Asn Asn Pro Lys Lys Lys Asn Lys Thr Arg Gly Ser Ser Gly

```
                35                  40                  45

Lys

<210> SEQ ID NO 125
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: A myristic acid and an aminohexanoic acid are
      added to the N-terminus during linear synthesis
<220> FEATURE:
<221> NAME/KEY: MISC_FEATURE
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 125

Ser Ser Cys Leu Ile Asp Ile Tyr Gly Val Cys His Asn Phe Asp Ala
1               5                   10                  15

Tyr Xaa His Lys Lys Asn Asn Pro Lys Lys Lys Asn Lys Thr Arg Gly
            20                  25                  30

Ser Ser Lys
        35

<210> SEQ ID NO 126
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 3 residues of aminoundecanoic acid ("AUD") are
      added sequentially to the N-terminus during linear synthesis
<220> FEATURE:
<221> NAME/KEY: MISC_FEATURE
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 126

Ser Ser Cys Leu Ile Asp Ile Tyr Gly Val Cys His Asn Phe Asp Ala
1               5                   10                  15

Tyr Xaa His Lys Lys Asn Asn Pro Lys Lys Lys Asn Lys Thr Arg Gly
            20                  25                  30

Ser Ser Lys
        35

<210> SEQ ID NO 127
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 4 residues of aminoundecanoic acid ("AUD") are
      added sequentially to the N-terminus during linear synthesis
<220> FEATURE:
<221> NAME/KEY: MISC_FEATURE
```

```
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 127

Ser Ser Cys Leu Ile Asp Ile Tyr Gly Val Cys His Asn Phe Asp Ala
1               5                   10                  15

Tyr Xaa His Lys Lys Asn Asn Pro Lys Lys Lys Asn Lys Thr Arg Gly
            20                  25                  30

Ser Ser Lys
        35

<210> SEQ ID NO 128
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 128

Ser Ser Cys Leu Ile Asp Ile Tyr Gly Val Cys His Asn Phe Asp Ala
1               5                   10                  15

Tyr Xaa Tyr Phe Arg Ala Phe Arg Lys Phe Val Lys Pro Phe Lys Arg
            20                  25                  30

Ala Phe Lys Gly Ser Ser Gly Lys
        35                  40

<210> SEQ ID NO 129
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: A myristic acid and an aminohexanoic acid are
      added to the N-terminus during linear synthesis
<220> FEATURE:
<221> NAME/KEY: MISC_FEATURE
<222> LOCATION: (18)..(18)
<223> OTHER INFORMATION: Residue 18 is a linker comprised of
      2 PEG [poly(ethylene) glycol] units having the shortest ether
      structure possible of PEG with two ethylene oxide unitsas follows:
      (HN-CH2-CH2-O-CH2-CH2-O-CH2-C=O)2

<400> SEQUENCE: 129

Ser Ser Cys Leu Ile Asp Ile Tyr Gly Val Cys His Asn Phe Asp Ala
1               5                   10                  15

Tyr Xaa Tyr Phe Arg Ala Phe Arg Lys Phe Val Lys Pro Phe Lys Arg
            20                  25                  30

Ala Phe Lys Gly Ser Ser Gly Lys
        35                  40

<210> SEQ ID NO 130
<211> LENGTH: 35
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 130

Ser Ser Cys Leu Ile Asp Ile Tyr Gly Val Cys His Asn Phe Asp Ala
1               5                   10                  15

Tyr Xaa His Lys Lys Asn Asn Pro Lys Lys Lys Asn Lys Thr Arg Gly
            20                  25                  30

Ser Ser Lys
        35

<210> SEQ ID NO 131
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Residue 18 is a linker comprised of 2 PEG
      [poly(ethylene) glycol] units having the shortest ether structure
      possible of PEG with two ethylene oxide unitsas follows:
      (HN-CH2-CH2-O-CH2-CH2-O-CH2-C=O)2

<400> SEQUENCE: 131

Ser Ser Cys Leu Ile Asp Ile Tyr Gly Val Cys His Asn Phe Asp Ala
1               5                   10                  15

Tyr Xaa Ser Ser His Arg Thr Asn His Lys Lys Asn Asn Pro Lys Lys
            20                  25                  30

Lys Asn Lys Thr Arg Gly Ser Ser Gly Lys
            35                  40
```

COMPOSITIONS AND METHODS FOR DELIVERY OF GLYCOPEPTIDE ANTIBIOTICS TO MEDICAL DEVICE SURFACES

CROSS REFERENCE TO RELATED APPLICATIONS

This patent application is a U.S. National Stage Filing under 35 U.S.C. 371 from International Patent Application Serial No. PCT/US2008/080321, filed Oct. 17, 2008, and published on Apr. 30, 2009, as WO 2009/055313 A1, which claims the priority benefit of U.S. Provisional Patent Application Ser. No. 60/981,565 filed Oct. 22, 2007 and U.S. Provisional Patent Application Ser. No. 61/056,746 filed May 28, 2008; each of which disclosures are incorporated herein by reference in their entireties.

GRANT STATEMENT

This presently disclosed subject matter was made in part from government support under Grant No. 1R43DE018584-01 from the National Institute of Dental and Craniofacial Research and Grant No. 9R44A1082540-02 from the National Institute of Allergy and Infectious Diseases. Thus, the U.S. Government has certain rights in the presently disclosed subject matter.

FIELD

The presently disclosed subject matter relates to compositions for delivery of glycopeptide antibiotics to a surface of a medical device. More particularly, the presently disclosed subject matter is directed to a family of peptides having binding affinity for a class of glycopeptide antibiotics, such peptides being useful in compositions and methods related to conferring antibacterial activity to one or more surfaces of a medical device.

BACKGROUND

The problems associated with adherence and growth of bacteria on medical devices are well known. For example, catheterization with a "central line catheter" involves placing polyurethane or polyvinylchloride tubing into a blood vessel in the patient's chest while the other end of the tubing remains exposed to the hospital room environment and therefore to a variety of pathogens, potentially including drug-resistant pathogens. Frequently, this catheterization results in the life-threatening complication of system-wide infection of the blood. Research suggests that up to 90% of such cases originate in films of bacteria that adhere to catheter walls. Other types of catheters that are frequently used include urinary catheters, which are typically used with incontinent elderly patients, and are typically made of silicone and latex. Unfortunately, virtually all patients who have urinary catheters in place for 28 days or more develop urinary tract infections. Nearly all hospital-acquired systemic infections that are not associated with central line catheters are associated with urinary catheters. Treatment of urinary catheter-associated infections alone costs an estimated $1.8 billion annually.

Similar problems currently exist with orthopedic implants. Main causes of orthopedic implant failure include host inflammatory responses, and infection due to the formation of bacterial biofilms on the surface of the implants. Furthermore, studies have shown that the rate of infection associated with external fixators can be as high as 85%. Because metal pins and wires are being used more often in the treatment of orthopedic trauma, primarily for external fixation of bone fractures, any device improvements that decrease the rate of infections from joint prostheses or other metallic implants could have a significant impact on the quality of orthopedic healthcare.

A wide variety of surface modifications to medical devices have been tried with a goal of reducing infection rates of the modified medical devices. Such surface modifications include encapsulation of the medical device with a polymer to retard adherence by bacteria, and impregnation or coating of the medical device with antimicrobial agents. Representative examples of patents involving articles that have been coated or impregnated with anti-microbial drugs include U.S. Pat. No. 5,520,664 ("Catheter Having a Long-Lasting Antimicrobial Surface Treatment"), U.S. Pat. No. 5,709,672 ("Silastic and Polymer-Based Catheters with Improved Antimicrobial/Antifungal Properties"), U.S. Pat. No. 6,361,526 ("Antimicrobial Tympanostomy Tubes"), U.S. Pat. No. 6,261,271 ("Anti-infective and antithrombogenic medical articles and method for their preparation"), U.S. Pat. No. 5,902,283 ("Antimicrobial impregnated catheters and other medical implants"), and U.S. Pat. No. 5,624,704 ("Antimicrobial impregnated catheters and other medical implants and method for impregnating catheters and other medical implants with an antimicrobial agent").

A functionally and structurally related class of glycopeptide antibiotics mediates antimicrobial activity by binding to the terminal D-alanine-D-alanine (D-Ala-D-Ala) of bacterial pentapeptide peptidoglycan precursors. This class of antibiotics has in common a three-dimensional structure containing a cleft into which binds peptide of highly specific configuration of D-Ala-D-Ala. Binding of D-Ala-D-Ala is believed to inhibit transpeptidation (cross-linking of D-Ala moiety with moieties on neighboring pentapeptides), thereby inhibiting cell wall growth. Antibiotics in this class of glycopeptide antibiotics include, but are not limited to vancomycin, avoparcin, ristocetin, teicoplanin, and their derivatives. For example, derivatives of vancomycin include, but are not limited to, multivalent vancomycins, pegylated vancomycin conjugates, norvancomycin, vancomycin disulfides, synmonicin, mono- or di-dechlorovancomycin, glutamine analogs of vancomycin (e.g., A51568B, and M43G), aspartic acid analogs of vancomycin (e.g., M43F, M43B), desvancosamine derivatives of vancomycin (e.g., A51568A and M43A, and corresponding aglycones), chlorine derivatives of vancomycin (e.g., A82846B, A82846A (eremomycin), orienticin A, A82846C), benzylic amino sugar derivatives of vancomycin (e.g., A82846B), N-acyl vancomycins, N-aracyl vancomycins, N-alkyl vancomycins (including but not limited to octylbenzyl, octyloxybenzyl, butylbenzyl, butyloxybenzyl, and butyl, derivatives). For a review of vancomycin-related glycopeptides, see, e.g., Nagarajan, *Antimicrob. Agents Chemother.* 1991, 35:605-609. Similar derivatives can be made using avoparcin, ristocetin, or teicoplanin, and methods well known in the art.

The need remains for a coating composition that can be applied to a medical device surface to inhibit growth of microorganisms. In addition, there remains a need for improved systems for localized delivery and extended release of antibiotics from surfaces of medical devices.

SUMMARY

The presently disclosed subject matter provides compositions and methods for delivering glycopeptide antibiotics to the surface of medical devices. In one embodiment, a peptide composition is provided comprising a glycopeptide antibiotic binding peptide having a glycopeptide antibiotic binding domain and binding affinity for a glycopeptide antibiotic. In one embodiment, the peptide composition further comprises a surface binding peptide having a surface binding domain and binding affinity for a surface material of which a medical device is comprised. In one embodiment, the glycopeptide antibiotic binding and surface binding peptides are coupled together. In one embodiment the peptide coupling is through a linker, wherein if the linker is absent, the peptides are linked directly together.

In one embodiment of the presently disclosed subject matter a method is provided for coating a medical device, the method comprising applying a peptide composition comprising a glycopeptide antibiotic binding peptide having a glycopeptide antibiotic binding domain and binding affinity for a glycopeptide antibiotic, wherein at least a portion of the peptide composition becomes bound to the surface of the medical device. In one embodiment, the peptide composition further comprises a surface binding peptide having a surface binding domain and binding affinity for a surface material of which a medical device is comprised, wherein at least a portion of the peptide composition becomes bound to the surface material of the medical device.

In one embodiment of the presently disclosed subject matter, a medical device is provided that is coated with a peptide composition comprising a glycopeptide antibiotic binding peptide having a glycopeptide antibiotic binding domain and binding affinity for a glycopeptide antibiotic. In one embodiment, the coated medical device further comprises a surface binding peptide having a surface binding domain and binding affinity for a surface material of the medical device.

In one embodiment of the presently disclosed subject matter, a kit is provided comprising a container containing a kit component, wherein the kit component comprises a glycopeptide antibiotic binding peptide having a glycopeptide antibiotic binding domain and binding affinity for a glycopeptide antibiotic. In one embodiment, the kit further comprises a surface binding peptide having a surface binding domain and binding affinity for a surface material of which a medical device is comprised, wherein the surface binding peptide can be coupled to the glycopeptide antibiotic binding peptide. Kits are also provided comprising additional components including a liquid for reconstitution, an applicator device, instructions for use, a medical device to which the peptide composition is to be applied, and combinations thereof.

DETAILED DESCRIPTION

The presently disclosed subject matter provides compositions and methods for delivering and localizing glycopeptide antibiotic to a surface of a medical device to prevent the growth of microbes. Preferably, release of the glycopeptide antibiotic from the surface of the medical device is over an extended period of time, for example, ranging from hours to days to weeks, such that antibiotic's activity can be retained at the site of the medical device.

DEFINITION SECTION

While the following terms are believed to be well understood by one of ordinary skill in the art, the following definitions are set forth to facilitate explanation of the presently disclosed subject matter.

The term "antibacterial activity" is used, for purposes of the specification and claims, to refer to the ability of a composition (including an antibiotic component thereof) to inhibit or irreversibly prevent bacterial growth. Such inhibition or prevention can be through a bactericidal action (the ability of the composition to kill, or irrevocably damage one or more species of bacteria susceptible to the antibiotic of the composition), or through a bacteriostatic action (the ability of the composition to inhibit the growth of one or more species of bacteria, without death of the one or more target bacterial species susceptible to the antibiotic of the composition), or via a combination thereof (e.g., if a combination of antibiotic compositions are used, with one or more being bactericidal, and one or more being bacteriostatic). Bactericidal or bacteriostatic action can be applied therapeutically (to an environment either presently exhibiting bacterial growth), or prophylactically (to an environment at risk of sustaining or supporting bacterial growth). When referring to the antibacterial activity conferred or imparted to a medical device coated by a composition according to the present subject matter, the primary activity is the ability to inhibit and/or prevent bacterial growth on the coated surface of the medical device by a mechanism of action comprising inhibiting cell wall growth.

The term "glycopeptide antibiotic" is used herein for purposes of the specification and claims, and as known to those skilled in the art, to mean an antibiotic with a mechanism of action comprising inhibiting bacterial cell wall growth. Antibiotics in this class of glycopeptide antibiotics include, but are not limited to vancomycin, avoparcin, ristocetin, teicoplanin, and their derivatives. For example, derivatives of vancomycin include, but are not limited to, multivalent vancomycins, pegylated vancomycin conjugates, norvancomycin, vancomycin disulfides, synmonicin, mono- or di-dechlorovancomycin, glutamine analogs of vancomycin (e.g., A51568B, and M43G), aspartic acid analogs of vancomycin (e.g., M43F, M43B), desvancosamine derivatives of vancomycin (e.g., A51568A and M43A, and corresponding aglycones), chlorine derivatives of vancomycin (e.g., A82846B, A82846A (eremomycin), orienticin A, A82846C), benzylic amino sugar derivatives of vancomycin (e.g., A82846B), N-acyl vancomycins, N-aracyl vancomycins, N-alkyl vancomycins (including but not limited to octylbenzyl, octyloxybenzyl, butylbenzyl, butyloxybenzyl, and butyl, derivatives). Similar derivatives can be made using avoparcin, ristocetin, or teicoplanin, and methods well known in the art. A preferred teicoplanin derivative includes, but is not limited to, dalbavancin.

The terms "first" and "second" are used herein for purposes of the specification and claims for ease of explanation in differentiating between two different molecules, and are not intended to be limiting the scope of the present subject matter, nor imply a spatial, sequential, or hierarchical order unless otherwise specifically stated.

The term "medical device", as used herein for purposes of the specification and claims, refers to a structure that is positioned or positionable into or onto an individual's body to prevent, treat, modulate or ameliorate damage or a disorder or disease or condition, repair or restore a function of a damaged tissue, or to provide a new function. A medical device can be created using any biocompatible material. Representative medical devices include, but are not limited to: hip endoprostheses, artificial joints, jaw or facial implants, dental implants, tendon and ligament replacements, skin replacements, bone fixation implants, metal replacements and metal screws, prosthetic plates, metal nails or pins or rivets, metal graft devices, polymer-containing grafts, vascular prostheses (e.g., patches (e.g., heart patches), annuloplasty rings, annular rings, mechanical assist devices, vascular sealing devices, peripheral venous catheters, central venous catheters, arterial catheters), defibrillators, guidewires, embolic protection filters and devices, implantable infusion pumps, vascular grafts, heart pacemakers, artificial heart valves, blood filters, closure devices (e.g., for closure of wounds, incisions, or defects in tissues, including but not limited to skin and other organs (heart, stomach, liver, etc.)), sutures, breast implants, penile implants, stents, catheters, shunts, nerve growth guides, leads for battery-powered medical devices, intraocular lenses, wound dressings, tissue sealants, aneurismal coils, prostheses (e.g., cochlear implants, visual prostheses (including, but not limited to, contact lenses, and other visual aid devices), joint prosthesis, dental prosthesis), neurostimulators, muscular stimulators, ophthalmic devices (glaucoma shunts, ophthalmic inserts, intraocular lenses, overlay lenses, ocular inserts, optical inserts), nebulizers, any article used as a conduit (e.g., a catheter, tubing (e.g., endotracheal tube, chest tube, and the like)) related to medical treatment or for biological materials (e.g., tubes for feeding, tubes for draining biological fluids); or any container used as a storage device for biological materials (e.g., biological fluid collection bags, devices for storing proteins or solutions containing cells, and the like). Medical devices can be comprised of one or more substrates including, but not limited to, metals (including metal alloys, metal oxides, etc.), polymers, non-metal oxides (e.g., crystalline oxides), ceramic, collagen-based substrates, and combinations or composites thereof.

The term "metal" is used herein for purposes of the specification and claims to mean one or more compounds or compositions comprising a metal represented in the Periodic Table (e.g., a transition metal, alkali metals, and alkaline earth metals, each of these comprise metals related in structure and function, as classified in the Periodic Table), a metal alloy, a metal oxide, and bioactive glass. Examples of preferred metals include, but are not limited to, titanium, titanium alloy, stainless steel, aluminum, zirconium alloy metal substrate (e.g., Oxinium™), cobalt chromium alloy, gold, silver, rhodium, zinc, tungsten, platinum, rubidium, and copper. A preferred type or composition of metal can be used in accordance with the presently disclosed subject matter to the exclusion of a type or composition of metal other than the preferred type or composition of metal.

The term "polymer" is used herein for purposes of the specification and claims to mean a molecule or material comprised of repeating structural units (a structural unit typically referred to as a monomer) connected by covalent chemical bonds. Depending on its intended use, a polymer can be biodegradable. Biodegradable polymers include, but are not limited to, for example, polymers that are self-dissolving, bioresorbable and/or degradable in vivo. In addition, polymers can be those that are non-biodegradable and/or synthetic (i.e., manufactured, and not found in nature). Further polymers of the presently disclosed subject matter include those polymers that are natural (i.e. found in nature, as made in living tissues of plants and/or animals).

Non-limiting examples of suitable synthetic polymers described as being biodegradable include: poly-amino acids; polyanhydrides including maleic anhydride polymers; polycarboxylic acid; some polyethylenes including, but not limited to, polyethylene glycol, polyethylene oxide; polypropylenes, including, but not limited to, polypropylene glycol, polypropylene fumarate; one or more of polylactic acid or polyglycolic acid (and copolymers and mixtures thereof, e.g., poly(L-lactic acid) (PLLA), poly(D,L,-lactide), poly(lactic acid-co-glycolic acid), 50/50 (DL-lactide-co-glycolide)); polyorthoesters; polydioxanone; polyphosphazenes; poly-depsipeptides; one or more of polycaprolactone (and co-polymers and mixtures thereof, e.g., poly(D,L-lactide-co-caprolactone) or polycaprolactone co-butylacrylate; polyhydroxybutyrate valerate and blends; some polycarbonates (e.g., tyrosine-derived polycarbonates and arylates, polyiminocarbonates, polydimethyltrimethylcarbonates); calcium phosphates; cyanoacrylate; some polyamides (including nylon); polyurethane; synthetic cellulosic polymers (e.g, cellulose acetate, cellulose butyrate, cellophane); and mixtures, combinations, and copolymers of any of the foregoing. Representative natural polymers described as being biodegradable include macromolecules (such as polysaccharides, e.g., alginate, starch, chitosan, cellulose, or their derivatives (e.g., hydroxypropylmethyl cellulose); proteins and polypeptides, e.g., gelatin, collagen, albumin, fibrin, fibrinogen); polyglycosaminoglycans (e.g. hyaluronic acid, chondroitin sulfate); and mixtures, combinations, composites (e.g., composite collagen-polymer substrates), and copolymers of any of the foregoing. A collagen-based substrate can include a composite collagen-polymer substrate, or a matrix comprised of collagen (e.g., including, but not limited to, demineralized bone matrix).

Non-limiting examples of suitable synthetic polymers described as being non-biodegradable include: inert polyaryletherketones, including polyetheretherketone ("PEEK"), polyether ketone, polyetherketoneketone, and polyetherketoneetherketoneketone; polyurethanes; polystyrene, and styrene-ethylene/butylene-styrene block copolymers; polyisobutylene copolymers and styrene-isobutylene-styrene block copolymers; polyvinylpyrrolidone; polyvinyl alcohols; copolymers of vinyl monomers; polyvinyl ethers; polyvinyl aromatics; polyethylene oxides; polyesters including polyethylene terephthalate; some polyamides; polyacrylamides; polyethers including polyether sulfone; polyalkylenes including polypropylene, polyethylene; copolymers of ethylene and polypropylene; some polycarbonates, silicone and silicone rubber; siloxane polymers; polytetrafluoroethylene; expanded polytetrafluoroethylene (e-PTFE); nylons and related polyamide copolymers; nylon; fluorinated ethylene propylene; hexafluororopropylene, polymethylmethacrylate (PMMA); 2-hydroxyethyl methacrylate (PHEMA); polyimides; polyethyleneterephthalate; polysulfone, and polysulfides; and mixtures, combinations, and copolymers (including cross-linked copolymers) of any of the foregoing.

The term "ceramic" is used herein for purposes of the specification and claims to mean inorganic non-metallic materials whose formation is due to the action of heat. Suitable ceramic materials include but are not limited to silicon oxides, aluminum oxides, alumina, silica, hydroxyapatites, glasses, quartz, calcium oxides, calcium phosphates, indium tin oxide (ITO), polysilanols, phosphorous oxide, porcelains, and combinations thereof.

The phrase "binding affinity" is used, for the purposes of the specification and claims, to refer to the ability of a peptide (as described herein) to have a binding affinity that is greater for one target molecule or surface material over another; e.g., an affinity for a given molecule in a heterogeneous population of molecules. For example, a peptide has binding affinity for a glycopeptide antibiotic when the peptide demonstrates preferential binding to glycopeptide antibiotic, as compared to binding to another non-glycopeptide type of antibiotic. As another example, a peptide has binding affinity for a surface comprising a metal when the peptide demonstrates preferential binding to metal, as compared to binding to another surface material such as a polymer. Such preferential binding can be dependent upon the presence of a particular conformation, structure, and/or charge on or within the peptide and/or material for which it has binding affinity. In some embodiments, a peptide that has binding affinity for a surface material or a glycopeptide antibiotic binds with at least 10% greater affinity, or 20%, 30%, 40%, 50%, 60%, 70%, 80%, 90%, 100%, 200%, 300%, 400% or 500% greater affinity, or a higher percentage, than the peptide binds to, for example, a different surface material or a non-glycopeptide antibiotic. In a preferred embodiment, a peptide has a binding affinity that is characterized by a relative binding affinity as measured by an EC50 of 10 µM or less, and more preferably less than 1 µM and more preferably less than 100 nM. The EC50 can be determined using any number of methods known in the art, such as by generating a concentration response curve from a binding assay in which the concentration of the peptide is titered with a known amount of the substrate for which the peptide has binding affinity. In such case, the EC50 represents the concentration of peptide producing 50% of the maximal binding observed for that peptide in the assay.

A "glycopeptide antibiotic binding domain" as used herein refers to a peptide or amino acid chain having no less than about 6 amino acids and no more than about 30 amino acid residues in length and binding affinity for a glycopeptide antibiotic, wherein the amino acid chain can include naturally occurring amino acids, synthetic amino acids, genetically encoded amino acids, non-genetically encoded amino acids, modified and/or tagged amino acids, and combinations thereof; however, an antibody is specifically excluded from the scope and definition of a glycopeptide antibiotic binding domain of the presently disclosed subject matter. In some embodiments, the glycopeptide antibiotic binding domain can have no less than about 7 amino acids and no more than about 25 amino acid residues in length, or no less than about 8 amino acids and no more than about 20 or 22 amino acid residues in length. In some embodiments, the glycopeptide antibiotic binding domain can have no less than about 9 amino acids and no more than about 18 or 19 amino acid residues in length, or no less than about 10 amino acids and no more than about 16 or 17 amino acid residues in length. The glycopeptide antibiotic peptide binding domain according to the presently disclosed subject matter comprises a contiguous sequence of no less than about 6 amino acids and no more than about 25 amino acids in length, and more preferably comprises 6, 7, 8, 9, 10, 11, 12, 13, 14, 15, 16, 17, 18, 19, 20, 21, 22, 23, 24 or 25 amino acids in length.

A "surface binding domain" as used herein refers to a peptide or amino acid chain having no less than about 7 amino acids and no more than about 30 amino acid residues in length and binding affinity for a surface material of a medical device; wherein the amino acid chain can include naturally occurring amino acids, synthetic amino acids, genetically encoded amino acids, non-genetically encoded amino acids, modified and/or tagged amino acids, and combinations thereof; however, an antibody is specifically excluded from the scope and definition of a surface binding domain of the presently disclosed subject matter. In some embodiments, the surface binding domain can have no less than about 8 amino acids and no more than about 25 amino acid residues in length, or no less than about 9 amino acids and no more than about 20 or 22 amino acid residues in length. The surface binding domain according to the presently disclosed subject matter comprises a contiguous sequence of no less than about 7 amino acids and no more than about 25 amino acids in length, and more preferably comprises 7, 8, 9, 10, 11, 12, 13, 14, 15, 16, 17, 18, 19, 20, 21, 22, 23, 24 or 25 amino acids in length.

The terms "peptide coating composition" or "peptide composition", for purposes of the specification and claims, refer to a composition comprising a peptide comprising a glycopeptide antibiotic binding domain according to the presently disclosed subject matter. In some embodiments, the peptide coating composition can further comprise a surface binding domain according to the presently disclosed subject matter. The coupling of the glycopeptide antibiotic binding domain peptide to the surface binding domain peptide can occur in either orientation. For example, the glycopeptide antibiotic binding domain peptide can occur at either the amino- or the carboxyl-terminus of the peptide composition. The peptide composition can further comprise bound glycopeptide antibiotic and one or more of a linker coupled to one or both peptide binding domains according to the presently disclosed subject matter, one or more amino- and/or carboxyl-terminal modifications according to the presently disclosed subject matter, a pharmaceutically acceptable carrier, and a combination thereof.

Thus, in one embodiment, a peptide composition of the presently disclosed subject matter can be represented by formula I: GABP-L-SBP or SBP-L-GABP, wherein GABP is a peptide of 6 to 50 amino acids comprising (i) a glycopeptide antibiotic binding domain of 6 to 30 amino acids and (ii) binding affinity for a glycopeptide antibiotic. SBP is a peptide of 7 to 50 amino acids comprising (i) a surface binding domain of 7 to 30 amino acids and (ii) binding affinity for a surface material of a medical device, and wherein SBP can be present or absent. L is a linker between SBP and GABP and L can be present or absent. If L is absent and SBP present, GABP and SBP are linked directly together. Preferably, the surface material of the medical device is selected from the group consisting of metal, nonmetal oxide, ceramic, polymer, and a combination thereof.

SBP can be coupled to GABP in such a way that each retains its respective binding affinity. Such coupling can include forming a multimeric molecule having two or more peptides having surface binding affinity for a medical device, two or more peptides having binding affinity for glycopeptide antibiotic, and a combination thereof. For example, using standard reagents and methods known in the art of peptide chemistry, two peptides can be coupled via a side chain-to-side chain bond (e.g., where each of the peptides has a side chain amine (e.g., such as the epsilon amine of lysine)), a side chain-to-N terminal bond (e.g., coupling the N-terminal amine of one peptide with the side chain amine of the other peptide), a side chain-to-C-terminal bond (e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, a peptide having surface binding affinity for a medical device can be coupled directly to a peptide having glycopeptide antibiotic binding affinity by synthesizing or expressing both peptides as a single peptide. The coupling of two or more peptides can also be via a linker to form a composition according to the presently disclosed subject matter.

Peptides according to the presently disclosed subject matter can in some embodiments include any pharmaceutical acceptable salt or ester thereof. A peptide used in accordance with the presently disclosed subject matter can be produced by chemical synthesis, enzymatic synthesis, recombinant expression, biochemical or enzymatic fragmentation of a larger molecule, chemical cleavage of larger molecule, a combination of the foregoing or, in general, made by any other method in the art, and preferably isolated. The term "isolated" means that the peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes.

Peptides and/or amino acids of the presently disclosed subject matter can include L-form amino acids, D-form amino acids, or a combination thereof. Representative non-genetically encoded amino acids include but are not limited to 2-aminoadipic acid; 3-aminoadipic acid; β-aminopropionicacid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

Further, a peptide according to the presently disclosed subject matter can be modified, such as by addition of chemical moieties, or substitutions, insertions, and deletions of amino acids, where such modifications provide for certain advantages in its use. Thus, the term "peptide" encompasses any of a variety of forms of peptide derivatives including, for example, amides, conjugates with proteins, cyclic peptides, polymerized peptides, conservatively substituted variants, analogs, fragments, chemically modified peptides, and peptide mimetics. Any peptide derivative that has desired binding characteristics of the family of peptides according to the presently disclosed subject matter can be used in the practice of the presently disclosed subject matter. For example, a chemical group, added to the N-terminal amino acid of a synthetic peptide to block chemical reactivity of the amino terminus of the peptide, comprises an N-terminal group. Such N-terminal groups for protecting the amino terminus of a peptide are well known in the art, and include, but are not limited to, lower alkanoyl groups, acyl groups, sulfonyl groups, and carbamate forming groups. Preferred N-terminal groups can include acetyl, Fmoc, and Boc. A chemical group, added to the C-terminal amino acid of a synthetic peptide to block chemical reactivity of the carboxy terminus of the peptide, comprises a C-terminal group. Such C-terminal groups for protecting the carboxy terminus of a peptide are well known in the art, and include, but are not limited to, an ester or amide group. Terminal modifications of a peptide are often useful to reduce susceptibility by proteinase digestion, and to therefore prolong a half-life of peptides in the presence of biological fluids where proteases can be present. Terminal modifications of a peptide can also include fatty acids modifications. Optionally, a peptide, as described herein, can comprise one or more amino acids that have been modified to contain one or more chemical groups (e.g., reactive functionalities such as fluorine, bromine, or iodine) to facilitate linking the peptide to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides that are useful in a composition according to the presently disclosed subject matter include peptides having a sequence according to SEQ ID NOs: 6-8 and peptides having one or more substitutions, additions and/or deletions of residues relative to the sequence of an exemplary peptide disclosed in Tables 1 & 4 and SEQ ID NOs: 1-5, 9-10, 14-120, and 124-131 herein, so long as the binding properties of the original exemplary peptides are substantially retained. Thus, the presently disclosed subject matter includes peptides that differ from the exemplary sequences disclosed herein by about 1, 2, 3, 4, 5, 6, 7, or 8 amino acids (depending on the length of the exemplary peptide disclosed herein), and that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity can be calculated manually or it can be calculated using a computer implementation of a mathematical algorithm, for example, GAP, BESTFIT, BLAST, FASTA, and TFASTA, or other programs or methods known in the art. Alignments using these programs can be performed using the default parameters. A peptide having an amino acid sequence consisting essentially of a sequence of an exemplary peptide disclosed herein can have one or more different amino acid residues as a result of substituting an amino acid residue in the sequence of the exemplary peptide with a functionally similar amino acid residue (a "conservative substitution"); provided that peptide containing a conservative substitution will substantially retain the binding affinity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another; or the substitution of an aliphatic chain-containing amino acid with an aliphatic amino acid (e.g., methionine, lysine and arginine have an aliphatic part to the side chain, and alanine, leucine, isoleucine, and valine are aliphatic amino acids).

In another embodiment, the peptides of the presently disclosed subject matter include the exemplary peptide binding domains disclosed in Tables 1 & 4 and SEQ ID NOs: 1-10, 14-119, and 124-131 that can comprise additional amino acids at the carboxyl and/or amino terminal ends (e.g., ranging from 1 to up to about 10, 20, 30 or 40 additional amino acids at one or both ends) so long as the binding properties of the original exemplary peptides are substantially retained. For example, the peptides comprising additional amino acids at one or both ends retain glycopeptide antibiotic binding affinity and/or surface-binding affinity as described herein. For example, peptides comprising additional amino acids at one or both ends of the exemplary amino acid sequences illustrated as SEQ ID NOs: 1-10, 14-120, and 124-131 will possess binding affinity for glycopeptide antibiotic and/or surface-binding affinity as provided herein, and will not possess any characteristics which constitutes a significant change in binding affinity (e.g., a significant change comprising greater than about a 10- to 50-fold or more difference in binding affinity).

The term "linker" is used, for purposes of the specification and claims, to refer to a compound or moiety that acts as a molecular bridge to covalently couple at least two different molecules (e.g., with respect to the presently disclosed subject matter, coupling at least one peptide having binding affinity for glycopeptide antibiotic to a surface of a medical device, or to a peptide having binding affinity for a surface material of a medical device). Thus, for example, one portion (e.g., a "first" reactive functionality) of the linker binds to at least one peptide having binding affinity for a surface, and another portion (e.g., a "second" reactive functionality) of the linker binds to a peptide having binding affinity for glycopeptide antibiotic. As known to those skilled in the art, and using methods known in the art, two molecules can be coupled to the linker in a step-wise manner, or can be coupled simultaneously to the linker. There is no particular size or content limitations for the linker so long as it can fulfill its purpose as a molecular bridge, and that the binding affinity of the peptide in a composition according to the presently disclosed subject matter is substantially retained.

Linkers are known to those skilled in the art to include, but are not limited to, chemical chains, chemical compounds (e.g., reagents), and the like. The linkers can include, but are not limited to, homobifunctional linkers and heterobifunctional linkers. Heterobifunctional linkers, well known to those skilled in the art, contain one end having a first reactive functionality (chemical group or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) can be employed as a linker with respect to the presently disclosed subject matter. In one embodiment, representative peptide linkers comprise multiple reactive sites to be coupled to a binding domain (e.g., polylysines, polyornithines, polycysteines, polyglutamic acid and polyaspartic acid) or comprise substantially inert peptide linkers (e.g., lipolyglycine, polyserine, polyproline, polyalanine, and other oligopeptides comprising alanyl, serinyl, prolinyl, and/or glycinyl amino acid residues). Linkers can also utilize copper-catalyzed azide-alkyne cycloaddition (e.g., "click chemistry") or any other methods well known in the art. Linkers are known in the art and include linkers that can be cleaved (e.g., by heat, by natural enzymes found in or on the body of an individual, and/or by pH sensitivity), and linkers that can be made reactive toward other molecular moieties or toward themselves, for cross-linking purposes. Examples of pH-sensitive materials useful as linkers can include, but are not limited to, cellulose acetate phthalate, cellulose acetate trimellitate, polyvinyl acetate phthalate, hydroxypropyl methylcellulose phthalate, and hydroxypropyl methylcellulose acetate succinate. Depending on such factors as the molecules to be linked, and the conditions in which the linking is performed, the linker can vary in length and composition for optimizing such properties as preservation of biological function, stability, resistance to certain chemical and/or temperature parameters, and of sufficient stereo-selectivity or size. For example, the linker should not significantly interfere with the ability of a composition to sufficiently bind to a surface or to a glycopeptide antibiotic, with appropriate avidity for the purpose. A preferred linker can be a molecule having activities that enhance or complement the function of the composition of the presently disclosed subject matter.

Suitable polymeric linkers are known in the art, and can comprise a synthetic polymer or a natural polymer. Representative synthetic polymers include but are not limited to polyethers (e.g., poly(ethylene glycol) ("PEG"), 10 unit poly (ethylene glycol) ("P10"), mini-PEG which is Fmoc-8-Amino-3,6-Dioxaoctanoic Acid ("MP")), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 daltons to about 20,000 kilodaltons (for constituent monomers). Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto(amido)carboxylic acid, an acrylamidocarboxylic acid, an acrlyamido-amidotriethylene glycolic acid, 7-aminobenzoic acid, and derivatives thereof.

In another embodiment, the linkers of the presently disclosed subject matter can be fatty acids. The fatty acids of the presently disclosed subject matter include saturated and unsaturated fatty acids such as but not limited to butyric acid, caproic acid, caprylic acid, capric acid, undecanoic acid, aminoundecanoic acid (AUD), lauric acid, myristic acid, palmitic acid, stearic acid, arachidic acid, behenic acid, lignoceric acid, eicosanoic acid, docosanoic acid, tetracosanoic acid, myristoleic acid, palmitoleic acid, oleic acid, linoleic acid, α-linolenic acid, arachidonic acid, eicosapentaenoic acid, erucic acid, and docosahexaenoic acid. For example, in some embodiments, the fatty acid linkers are used as a linking group between the surface-binding peptide and the glycopeptide antibiotic binding peptide. In addition to their use as linkers, the fatty acid molecules of the presently disclosed subject matter can be used in other embodiments to modify the surface-binding peptide and the glycopeptide antibiotic binding peptide. For example, in some embodiments fatty acids are used to modify the amino- and/or the carboxyl-terminal end of the peptide compositions comprising surface-binding and glyocpeptide antibiotic binding peptides.

The term "pharmaceutically acceptable carrier", when used herein for purposes of the specification and claims, means a carrier medium that is a suitable support medium for administration and/or application of a composition according to the present subject matter. Preferably, a pharmaceutically acceptable carrier does not significantly alter the biological activity of the composition according to the presently disclosed subject matter to which it is added. Examples of such a carrier medium include, but are not limited to, aqueous solutions, aqueous or non-aqueous solvents, suspensions, emulsions, gels, pastes, and the like. As known to those skilled in the art, a suitable pharmaceutically acceptable carrier can comprise one or substances, including but not limited to, water, buffered water, medical parenteral vehicles, saline, 0.3% glycine, aqueous alcohols, isotonic aqueous buffer; and can further include one or more substances such as water-soluble polymer, glycerol, polyethylene glycol, glycerin, oils, salts such as sodium, potassium, magnesium and ammonium, phosphonates, carbonate esters, fatty acids, saccharides, polysaccharides, glycoproteins (for enhanced stability), excipients, and preservatives and/or stabilizers (to increase shelf-life or as necessary and suitable for manufacture and distribution of the composition).

The term "effective amount" is used herein, in relation to a composition according to the presently disclosed subject matter and a medical device to which it binds or is coupled, and for purposes of the specification and claims, to mean an amount sufficient of the composition so as to mediate binding of the composition to the substrate; in promoting attachment of the composition to a medical device. The term "effective amount" is used herein, in referring to use of a composition according to the presently disclosed subject matter and its antibacterial activity, and for purposes of the specification and claims, to mean an amount of glycopeptide antibiotic in the composition effective for inhibiting bacterial growth at the surface of the medical device to which it is applied.

The term "individual", as used herein for purposes of the specification and claims, refers to either a human or an animal, and preferably a human.

The presently disclosed subject matter provides peptides having binding affinity for glycopeptide antibiotic; compositions comprising the peptides according to the presently disclosed subject matter; methods for coating medical devices by applying the peptide compositions of the presently disclosed subject matter; and medical devices onto which a peptide composition according to the presently disclosed subject matter has been applied. Exemplary peptides having binding affinity for glycopeptide antibiotic comprise a peptide selected from the group consisting of an amino acid selected from the group consisting of SEQ ID NOs: 1-10 and 119, 124-131, a peptide having 95% identity with any one or more of SEQ ID NOs: 1-10 and 119, 124-131, a conservatively substituted variant thereof, a modified peptide thereof (i.e., the peptide being modified to comprise one or more of a terminal modification, and a modification to facilitate linking), and a combination thereof.

The following examples are provided to further describe certain aspects of the presently disclosed subject matter and are not intended to limit the scope of the presently disclosed subject matter.

EXAMPLE 1

Phage display technology is commonly used to generate a peptide having binding affinity typically mediated by a protein-peptide interaction. Phage display has been also used successfully to generate peptides having binding affinity for surface materials (e.g., metal surface, or polymer surface). However, phage display has not been typically used successfully to generate a peptide having high binding affinity (e.g., as measured by an EC50 of less than <1 mM) for a small molecule (e.g., having a molecular size under 2,000 daltons, and more typically, under 1,500 daltons) such as vancomycin. Thus, Illustrated in this Example are various methods for utilizing phage display technology to unexpectedly produce a peptide having binding affinity (including high binding affinity) for glycopeptide antibiotic. Peptides having binding affinity for a surface of a medical device were initially developed using solid phase screening and phage display techniques as previously described, followed by peptide design and peptide synthesis resulting in improved binding properties.

As compared to previously described methods for phage selection, it was unexpectedly discovered during the development of the presently disclosed subject matter that phage displaying peptides were successfully obtained having binding affinity for vancomycin and other glycopeptide antibiotics.

As an illustrative example of methods used in development of this presently disclosed subject matter, an aliquot of biotinylated vancomycin (100 pmoles) in buffer-T (200 µl, 0.05 M Tris-buffered saline, with TWEEN-20 at a final concentration of 0.05%) was dispensed in a series of microfuge tubes. Added per tube was 25 µl of a mixture of phage libraries to be screened (e.g., at a concentration of $10^{10}$ pfu/ml each), and the mixture was incubated at room temperature for 2 hours. To the mixture was added streptavidin-labeled metal beads which had been blocked with 1% bovine serum albumin (BSA) in buffer-T, and the bead-containing mixture was gently mixed for 2 hours at room temperature. The tubes were then washed 3 times with 1 ml of buffer-T+0.5 mM biotin, using magnetism to pull down the metal beads each time. The supernatant was removed, and phage was eluted from the metal beads by competition with vancomycin. In the elution process, added to each tube containing the beads was 20 µl of 0.1 mM vancomycin, and the bead-containing mixture was incubated at room temperature for 20 minutes. The phage-containing supernatant was then transferred to cultures of *E. coli* cells susceptible to phage infection, and incubated overnight at 37° C. in a shaker incubator. Phage supernatant was harvested by centrifugation of culture medium at 8500×g for 10 minutes. Second and third rounds of selection were performed in a similar manner to the first round, using the amplified phage from the previous round as input.

For determining phage binding, an ELISA (enzyme-linked immunoassay) was performed as follows. Wells of a microtiter plate were coated with streptavidin by incubating 50 µl of a 10 µg/ml solution per well for 16 hours and at 4° C. Non-specific binding sites on the well surfaces of the microtiter plate were blocked with 250 µl 1% BSA in 0.1 M $NaHCO_3$. The plate was incubated for at least 2 hours at room temperature. After washing the wells 3 times with buffer-T, to each well was added biotinylated vancomycin (0.1 µM) in 100 µl buffer-T and incubated for 30 minutes at room temperature. Biotin (0.1 µM) in 100 µl buffer-T was then added to each well, to block any available streptavidin sites. The plate was incubated for 30 minutes at room temperature, followed by 5 washes with buffer-T. To each well was added 175 µl of buffer-T and 25 µl of the phage solution being tested, followed by incubation at room temperature for 2 hours. Following several washes with buffer-T, added was anti-M13 phage antibody conjugated to horseradish-peroxidase, followed by incubation, and washing. Added was chromogenic agent ABTS (2,2'-azino-bis(3-ethylbenzthiazoline-6-sulphonic acid), and determined was a read-out at 405 nm at 15 minutes. The resultant absorbance value for each well correlates to the amount of phage bound to vancomycin.

Primers against the phage vector sequence that flank the insertion site were used to determine the DNA sequence encoding the peptide for the phage in each group. The sequence encoding the peptide insert was translated to yield the corresponding amino acid sequence displayed on the phage surface. The amino acid sequences, encoding peptides isolated using vancomycin as the representative glycopeptide antibiotic, were determined and are shown in Table 1. While phage amino acids adjoining the peptides typically did not provide a significant contribution to the binding affinity of the peptide, the peptides according to the presently disclosed subject matter can comprise, in their amino acid sequence, phage amino acids adjoining the peptide at the N-terminus (SS) and at the C-terminus (SR). The peptide sequence shown in SEQ ID NO: 5 represents site directed mutagenesis of the first cysteine residue of SEQ ID NO: 1 to a serine residue.

The phage-derived sequences were further evaluated as synthetic peptides. Peptides according to the presently disclosed subject matter can be synthesized using any method known to those skilled in the art including, but not limited to, solid phase synthesis, solution phase synthesis, linear synthesis, recombinantly, and a combination thereof. In this example, peptides were synthesized using standard solid-phase peptide synthesis techniques on a peptide synthesizer using standard Fmoc chemistry. After all residues were coupled, simultaneous cleavage and side chain deprotection was achieved by treatment with a trifluoroacetic acid (TFA) cocktail. Crude peptide was precipitated with cold diethyl ether and purified by high performance liquid chromatography (HPLC) using a linear gradient of water/acetonitrile containing 0.1% TFA. Homogeneity of the synthetic peptides was evaluated by analytical reverse phase-HPLC, and the identity of the peptides was confirmed with mass spectrometry.

A typical binding assay for glycopeptide antibiotic was performed according to the following procedure. Briefly, synthetic peptides comprising an amino acid sequence to be characterized for binding were biotinylated to facilitate immobilization on streptavidin-coated 96-well plates. The microtiter plates were coated with streptavidin by adding 50 µl of a 10 µg/ml streptavidin solution in 0.1M NaHCO$_3$, and incubating the plates for at least 3 hours. The plate wells were blocked by adding 150 µl of a 1% BSA solution in 0.1 NaHCO$_3$ with incubation for at least 2 hours, and the plates were stored at 4° C. until needed. Before use, the streptavidin plates were washed extensively in buffer-T. Added per well was peptide (100 µl 0.1 µM peptide in buffer-T), and then incubated for 30 minutes at room temperature with shaking. 200 µl of 0.5 mM biotin in buffer-T was added to block the remaining streptavidin sites, and plates were incubated for 15 minutes at room temperature. Plates were then washed with buffer-T to remove the excess biotin and peptide. Serial dilutions of biotinylated glycopeptide antibiotic in buffer-T were added (100 µl) to each well, representing a range of concentrations between 100 pM and 100 µM. Plates were incubated for 30 minutes at room temperature with shaking prior to washing several times with buffer-T. Glycopeptide antibiotic was then detected by adding 100 µl of a diluted streptavidin-alkaline phosphatase conjugate to each well and incubated at room temperature for 30 minutes. Excess conjugate was removed by repeated washes with buffer-T, and the amount of alkaline phosphatase remaining in the well was detected using a pNPP (para-nitrophenylphosphate) colorimetric enzymatic assay. The relative amount of glycopeptide antibiotic captured by the peptides was determined by measuring the absorbance at 405 nm of the colored product of the alkaline phosphatase reaction. The EC50 was determined for each peptide relative to the binding affinity for the glycopeptide antibiotic used in the assay, as shown in Table 1 (with vancomycin as a representative glycopeptide antibiotic).

TABLE 1

Peptide sequences isolated by phage selections using vancomycin

| SEQ ID NO: | Amino acid sequence | EC50 (µM) for vancomycin binding |
|---|---|---|
| 1 | CLIDMYGVCHNFDGAYDS | 0.10 |
| 2 | CLFDIFGVCHSFDGAYDS | 0.06 |
| 3 | PCELIDMFGNDHCP | 0.82 |
| 4 | SCDMLFCENFSGSGNNWFS | 10 |
| 5 | SLIDMYGVCHNFDGAYDS | 10 |

To identify additional peptides capable of binding vancomycin, a scanning degenerate codon mutagenesis study was performed using SEQ ID NO: 1. To rapidly test variants of the isolated vancomycin binding peptide, a bacterial expression system was designed. Under this system, a peptide sequence was placed under the transcriptional control of a T7 promoter. The peptide was expressed with an N-terminal OmpA signal peptide, targeting it for secretion. An HA-tag was engineered downstream of the peptide sequence for antibody-mediated detection, a rhinovirus protease cleavage site was engineered for peptide liberation, and the DNA sequence encoding alkaline phosphatase was engineered for p-NPP colorimetric detection. Using this expression system, a scanning mutagenesis study was performed in which new peptide sequences were generated using mutagenic oligonucleotide primers and tested for vancomycin binding. The C-terminal His6 tag enabled the high-throughput peptide purification on Ni$^{2+}$ columns or beads (Qiagen; Cat#30600). After PCR mutagenesis and cloning of a sequence into the vector, competent cells were transformed and cultured overnight on 2xYT-KAN-BCIP (40 ug/ml) plates at 37° C. Transformed colonies were grown in 2xYT-KAN broth overnight. Peptide-AP fusion-containing supernatants were harvested and tested for binding to vancomycin. Briefly, the variant peptides were tested for vancomycin binding as follows. A streptavidin coated microtiter plate was coated with biotinylated vancomycin. The concentrations of the alkaline-phosphatase linked variant peptides were normalized to equal levels based on the alkaline-phosphatase activity as determined in a kinetic assay with the alkaline-phosphatase specific chromogenic substrate p-nitrophenyl phosphate (p-NPP). A streptavidin coated microtiter plate was coated with biotinylated vancomycin. Normalized amounts of alkaline-phosphatase linked peptides were allowed to bind to the immobilized vancomycin and detected by addition of the alkaline-phosphatase specific chromogenic substrate p-NPP. The results of the mutagenesis study are shown in Table 2.

TABLE 2

Scanning degenerate codon mutagenesis of SEQ ID NO: 1

| | Substitution | | |
|---|---|---|---|
| Position | Acceptable | Unacceptable | Reduced Binding |
| C1 | C | A E G P S V | |
| L2 | L M | C G P Q T | D K S W |
| I3 | I M | A G P S | L |
| D4 | D | E H S Y A | |
| M5 | M I | F H K R W V | |
| Y6 | Y | A D E G K N S V | |

TABLE 2-continued

Scanning degenerate codon mutagenesis of SEQ ID NO: 1

| | Substitution | | |
|---|---|---|---|
| Position | Acceptable | Unacceptable | Reduced Binding |
| G7 | G | A R S V | L E |
| V8 | V R K Q | C P | G S W D |
| C9 | C | D E G W | R |
| H10 | H | A E G K L M N P R T | |
| N11 | N D M S | C | G E |
| F12 | F E H K L P Q R S Y | | |
| D13 | D L T V | C | A Y |
| G14 | G R | | S A F K T V W Y |
| A15 | A G | C | P S |
| Y16 | Y M W G | | C L Y |
| D17 | D I L P | | |

From an alignment of the amino acid sequence of the peptides identified by phage selections using vancomycin as the illustrative glycopeptide antibiotic in Table 1, a consensus glycopeptide antibiotic binding domain sequence was constructed (SEQ ID NO: 6) representing all of SEQ ID NOs: 1-4 and taking into account the results of the mutagenesis study with SEQ ID NO: 1. The consensus glycopeptide antibiotic binding domain SEQ ID NO: 6 is as follows: $CXaa_{0-3}DMF-GXaa_{0-3}C$, (SEQ ID NO: 6), wherein Xaa represents any amino acid, the 2 cysteine residues are disulfide bonded, and the length between the 2 cysteine residues can range from 4 to 10 amino acids.

Similarly, from an alignment of the amino acid sequence of the peptides identified by phage selections using vancomycin as the illustrative glycopeptide antibiotic in Table 1, a consensus glycopeptide antibiotic binding domain sequence was constructed (SEQ ID NO: 7) representing all of SEQ ID NOs: 1-4 and taking into account the results of the mutagenesis study with SEQ ID NO: 1. The consensus glycopeptide antibiotic binding domain SEQ ID NO: 7 is as follows: $Xaa_1Xaa_2X_1X_2X_3X_4X_5X_6X_7Xaa_3X_8X_9$, (SEQ ID NO: 7), wherein the sequence comprises at least 2 cysteine residues; wherein Xaa is any amino acid unless stated otherwise; wherein either $Xaa_1$ or $Xaa_2$ is C and $Xaa_2$ can be absent if $Xaa_1$ is C; wherein $X_1$ is L, M, I, V or A; wherein $X_2$ is I, M or F; wherein $X_3$ is D; wherein $X_4$ is M or I; wherein $X_5$ is F or Y; wherein $X_6$ is G; wherein $X_7$ is any amino acid except C or P; wherein if $X_8$ or $X_9$ is C, $Xaa_3$ is any amino acid except C and can be absent; wherein $X_8$ is C or H unless $Xaa_3$ or $X_9$ is C and then $X_8$ is not C; and wherein $X_9$ is H or C unless $Xaa_3$ or $X_8$ is C and then $X_9$ is not C.

In another embodiment, a consensus glycopeptide antibiotic binding domain sequence was constructed (SEQ ID NO: 8) representing all of SEQ ID NOs: 1-5 and taking into account the results of the mutagenesis study with SEQ ID NO: 1 with SEQ ID NO: 1 shown in Table 2. The consensus glycopeptide antibiotic binding domain is as follows: $Xaa_1Xaa_2X_1X_2X_3X_4X_5X_6X_7Xaa_3X_8X_9$, (SEQ ID NO: 8) wherein the sequence comprises at least 2 cysteine residues; wherein Xaa is any amino acid unless stated otherwise; wherein either $Xaa_1$ or $Xaa_2$ is C and $Xaa_2$ can be absent if $Xaa_1$ is C; wherein $X_1$ is not C, G, P, Q or T; wherein $X_2$ is not A, G, P or S; wherein $X_3$ is D or C; wherein $X_4$ is M or I; wherein $X_5$ is F or Y; wherein $X_6$ is not A, R, S or V; wherein $X_7$ is any amino acid except C or P; wherein if $X_8$ or $X_9$ is C, $Xaa_3$ is any amino acid except C and can be absent; wherein $X_8$ is C or H unless $Xaa_3$ or $X_9$ is C and then $X_8$ is not C; and wherein $X_9$ is H or C unless $Xaa_3$ or $X_8$ is C and then $X_9$ is not C.

Thus, a peptide binding domain sequence motif is provided having binding affinity for glycopeptide antibiotic. A peptide according to the glycopeptide antibiotic binding domain of SEQ ID NOs: 6-8 can further comprise modifications according to the presently disclosed subject matter including, for example, one or more of a terminal modification, and a modification to facilitate linking of the peptide. Thus, such a peptide can have an amino acid sequence selected from the group consisting of SEQ ID NOs: 1-8. Preferably, the peptide according to the presently disclosed subject matter has a binding affinity for glycopeptide antibiotic of EC50 less than 1 μM.

EXAMPLE 2

In this example, illustrated are further characterizations of peptides according to the presently disclosed subject matter.

Structure-Function and Binding Affinity Characterizations

From the peptide amino acid sequence SSCLIDMYGVCHNFDGAYDSSR (SEQ ID NO: 1) additional peptides were designed and expressed in the bacterial expression system described herein to further evaluate structure-function relationships. A truncated peptide comprising the amino acid sequence of SEQ ID NO:9 (STCLIDMYGVCH) was expressed and compared to a peptide comprising SEQ ID NO:1 for binding affinity for glycopeptide antibiotic. Also produced were a dimer of this truncated peptide (SEQ ID NO:10; STCLIDMYGVCHSSCLIDMYGVCH), a D to A substitution (SEQ ID NO:11; STCLIAMYGVCH), a D to E substitution (SEQ ID NO:12; STCLIEMYGVCH), and a G to S substitution (SEQ ID NO:13; STCLIDMYSVCH). Relative binding strengths of these peptides and of other representative peptides to glycopeptide antibiotic were determined by EC50 values for binding to vancomycin or other glycopeptide antibiotic.

A typical binding assay for glycopeptide antibiotic was performed according to the following procedure. The concentrations of the alkaline-phosphatase linked variant peptides were normalized to equal levels based on the alkaline-phosphatase activity as determined in a kinetic assay with the alkaline-phosphatase specific chromogenic substrate p-nitrophenyl phosphate (p-NPP). A streptavidin coated microtiter plate was coated with biotinylated vancomycin. Serial dilutions of normalized alkaline-phosphatase linked peptides were allowed to bind to the immobilized vancomycin and detected by addition of the alkaline-phosphatase specific chromogenic substrate p-NPP. Relative affinity for peptide binding to the immobilized vancomycin was determined by measuring the absorbance at 405 nm of the colored product of the alkaline phosphatase reaction. For the alkaline-phosphatase linked peptides that displayed glycopeptide antibiotic binding (SEQ ID NOs: 9 & 10), synthetic peptides were synthesized. In contrast, no detectable glycopeptide antibiotic binding was observed for SEQ ID NOs: 11, 12 or 13. EC50 values for the synthetic peptides binding to vancomycin were determined as described in Example 1 and are shown in Table 3. Preferred are peptides that bind to glycopeptide antibiotic with binding affinity of EC50 of less than or equal to about 1 μM, and more preferably, in the nanomolar range (e.g., <0.1 μM).

TABLE 3

| Binding to glycopeptide antibiotic | |
| --- | --- |
| SEQ ID NO: | EC50 |
| 1 | <100 nM |
| 2 | <100 nM |
| 3 | <100 nM |
| 9 | <1 µM |
| 10 | <1 µM |

As evident from Table 3, a peptide comprising an amino acid sequence of SEQ ID NO:9 shows similar binding affinity for vancomycin as compared to a peptide comprising the amino acid sequence of SEQ ID NO:1, indicating that an amino acid sequence of SEQ ID NO:9 represents a core motif important for binding affinity to glycopeptide antibiotic. This core motif can also be represented by the consensus amino acid sequence illustrated as SEQ ID NOs: 6-8, and described in Example 1 herein. Also, as noted from Table 3, substitutions in the core motif at the D position (amino acid position 6 in SEQ ID NO: 9; see Table 3, SEQ ID NOs: 11 & 12) or at the G position (amino acid position 9 in SEQ ID NO: 9; see Table 3, SEQ ID NO: 13) resulted in loss of binding affinity to glycopeptide antibiotic, indicating the importance of these two residues at these key positions in the core motif in the function of binding to glycopeptide antibiotic. As may also be deduced from Table 3 and other data, concatamers of this core motif can show similar or improved binding to glycopeptide antibiotic as compared to a monomer of the core motif (see, Table 3, SEQ ID NOs: 9 & 10). Studies evaluating other substitutions in this core motif show that a cysteine disulfide bridge is preferred for optimal binding to glycopeptide antibiotic (e.g., two cysteines separated from about 7 to about 9 amino acids; see, e.g., cysteine residues at amino acid positions 3 and 11 of SEQ ID NO:9). Substitution of the disulfide bond with a thioether shows comparable binding to glycopeptide antibiotic as does the core motif with the disulfide bond.

The binding assays described herein, and other data suggest that in application of a peptide composition according to the presently disclosed subject matter to a surface material (such as of a medical device), a time sufficient for binding the peptide composition to the surface material (and for binding glycopeptide antibiotic to the composition) can comprise minimally several minutes of contacting the surface material with the composition. Thus, a time sufficient for binding can be in a range of from about 5 minutes to about 5 hours, from about 5 minutes to about 2 hours and from about 5 minutes to about 15 minutes.

Further Characterization of Binding Affinity

Using a similar binding assay format as described herein for vancomycin, the ability of a peptide comprising the amino acid sequence of SEQ ID NO: 1 to bind gentamycin (an aminoglycoside antibiotic) was determined. The results of this assay showed that this representative peptide lacked significant binding affinity for gentamycin.

As shown by Tables 1 & 3, and as described in more detail herein previously, the peptides of the presently disclosed subject matter are related in structure (e.g., amino acid sequence homology and/or identity) as well as function (e.g., have binding affinity for glycopeptide antibiotic such as vancomycin). It was found, by experimentation, that the binding of these peptides for vancomycin is inhibited by Lys-D-Ala-D-Ala. While not limiting the presently disclosed subject matter to a particular mechanism, this finding suggests that the peptides bind to vancomycin by binding the portion or conformational pocket of vancomycin that binds terminal D-Ala-D-Ala of bacterial pentapeptide peptidoglycan precursors. By virtue of this feature of binding affinity, it is suggested that the peptides according to the presently disclosed subject matter can bind to vancomycin, and other glycopeptide antibiotics that mediate antibacterial activity by binding to terminal D-Ala-D-Ala of bacterial pentapeptide peptidoglycan precursors.

As an example, illustrated is the inhibition by Lys-D-Ala-D-Ala of specific binding between vancomycin and a peptide comprising the amino acid sequence of SEQ ID NO:1. To the wells of a 96 well plate coated with streptavidin was added 100 µl of a 0.2 µM solution of biotinylated peptide in buffer-T. After incubation, the wells were blocked by adding 200 µl of a 0.5 mM solution of biotin in buffer-T. The plates were then washed three times with buffer-T. Serial dilutions of Lys-D-Ala-D-Ala were prepared, and added individually to the wells such that Lys-D-Ala-D-Ala ranged in a final concentration of from about 1 µM to about 200 µM (in a volume of 35 µl). Also added to each well was 35 µl of biotinylated vancomycin (20 nM final concentration), and the plate was incubated at 30 minutes for room temperature. The wells were then washed three times with buffer-T, followed by the addition of 100 µl of streptavidin-alkaline phosphatase conjugate (1 mg/ml diluted 1:500 in buffer-T). Following a 30 minute incubation, the wells were washed five times with buffer-T. Added to each well was 100 µl of pNPP, followed by colorimetric detection after 12 minutes at an absorbance of 405 nm. The results of the assay show that only about 10 µM of Lys-D-Ala-D-Ala is needed to inhibit about 50% of the binding between vancomycin and a peptide according to the presently disclosed subject matter having binding affinity for glycopeptide antibiotic; and close to 100% inhibition is achieved with a concentration of Lys-D-Ala-D-Ala of between 100 µM to 200 µM. Thus, it is suggested that Lys-D-Ala-D-Ala can inhibit the binding of a peptide according to the presently disclosed subject matter to glycopeptide antibiotic.

EXAMPLE 3

While other surface-binding peptides known in the art can be used as a component in a composition according to the presently disclosed subject matter to be coupled to a peptide according to the presently disclosed subject matter having binding affinity for glycopeptide antibiotic, Table 4 illustrates representative peptides having binding affinity for a surface material of a medical device ("surface-binding peptides"). For example, surface-binding peptides comprise amino acid sequences: SEQ ID NOs: 14-35 having binding affinity for polystyrene; SEQ ID NO:36 having binding affinity for polyurethane; SEQ ID NOs: 37-50 having binding affinity for polyglycolic acid; SEQ ID NOs: 51-56 having binding affinity for polycarbonate; SEQ ID NOs: 57-65 having binding affinity for nylon; SEQ ID NOs: 66 and 67 having binding affinity for TEFLON; SEQ ID NOs: 68 and 69 having binding affinity for polyethylene terephthalate fibers; SEQ ID NOs: 70 and 71 having binding affinity for collagen-based substrates; SEQ ID NOs: 72-119 having binding affinity for a metal (e.g., comprising one or more of titanium, and stainless steel). At least one surface-binding peptide can be coupled to at least one peptide having binding affinity for glycopeptide antibiotic in producing a composition according to the presently disclosed subject matter.

TABLE 4

Exemplary surface-binding peptides

| SEQ ID NO: | Amino acid sequence (single letter code) |
|---|---|
| | Binding affinity for polystyrene |
| 14 | FLSFVFPASAWGG |
| 15 | FYMPFGPTWWQHV |
| 16 | LFSWFLPTDNYPV |
| 17 | FMDIWSPWHLLGT |
| 18 | FSSLFFPHWPAQL |
| 19 | SCAMAQWFCDRAEPHHVIS |
| 20 | SCNMSHLTGVSLCDSLATS |
| 21 | SCVYSFIDGSGCNSHSLGS |
| 22 | SCSGFHLLCESRSMQRELS |
| 23 | SCGILCSAFPFNNHQVGAS |
| 24 | SCCSMFFKNVSYVGASNPS |
| 25 | SCPIWKYCDDYSRSGSIFS |
| 26 | SCLFNSMKCLVLILCFVS |
| 27 | SCYVNGHNSVWVVVFWGVS |
| 28 | SCDFVCNVLFNVNHGSNMS |
| 29 | SCLNKFFVLMSVGLRSYTS |
| 30 | SCCNHNSTSVKDVQFPTLS |
| 31 | FFPSSWYSHLGVL |
| 32 | FFGFDVYDMSNAL |
| 33 | LSFSDFYFSEGSE |
| 34 | FSYSVSYAHPEGL |
| 35 | LPHLIQYRVLLVS |
| | Binding affinity for polyurethane |
| 36 | SCYVNGHNSVWVVVFWGVS |
| | Binding affinity of polyglycolic acid |
| 37 | SCNSFMFINGSFKETGGCS |
| 38 | SCFGNLGNLIYTCDRLMPS |
| 39 | SCSFFMPWCNFLNGEMAVS |
| 40 | SCFGNVFCVYNQFAAGLFS |
| 41 | SCCFINSNFSVMNHSLFKS |
| 42 | SCDYFSFLECFSNGWSGAS |
| 43 | SCWMGLFECPDAWLHDWDS |
| 44 | SCFWYSWLCSASSSDALIS |
| 45 | SCFGNFLSFGFNCESALGS |
| 46 | SCLYCHLNNQFLSWVSGNS |
| 47 | SCFGFSDCLSWFVQPSTAS |
| 48 | SCNHLGFFSSFCDRLVENS |
| 49 | SCGYFCSFYNYLDIGTASS |
| 50 | SCNSSSYSWYCWFGGSSPS |
| | Binding affinity for polycarbonate |
| 51 | FGHGWLNTLNLGW |
| 52 | FSPFSANLWYDMF |
| 53 | VFVPFGNWLSTSV |
| 54 | FWNVNYNPWGWNY |
| 55 | FYWDRLNVGWGLL |
| 56 | LYSTMYPGMSWLV |
| | Binding affinity for nylon |
| 57 | SCFYQNVISSSFAGNPWEC |
| 58 | SCNMLLNSLPLPSEDWSAC |
| 59 | SCPFTHSLALNTDRASPGC |
| 60 | SCFESDFPNVRHHVLKQSC |
| 61 | SCVFDSKHFSPTHSPHDVC |
| 62 | SCGDHMTDKNMPNSGISGC |
| 63 | SCDFFNRHGYNSGCEHSVC |
| 64 | SCGDHMTDKNMPNSGISGC |
| 65 | SCYYNGLVVHHSNSGHKDC |
| | Binding affinity for TEFLON |
| 66 | CWSRFRLFMLFCMFYLVS |
| 67 | CIKYPFLYCCLLSLFLFS |
| | Binding affinity for polyethylene terephthalate fibers |
| 68 | SWWGFWNGSAAPVWSR |
| 69 | SWDFRSLRDWWPPAPSLSSR |
| | Binding affinity for collagen-based substrates |
| 70 | SIFSTWNPWSPYSVSR |
| 71 | SFGSWWWGSGAASSR |
| | Binding affinity for titanium |
| 72 | SCFWFLRWSLFIVLFTCCS |
| 73 | SCESVDCFADSRMAKVSMS |
| 74 | SCVGFFCITGSDVASVNSS |

TABLE 4-continued

Exemplary surface-binding peptides

| SEQ ID NO: | Amino acid sequence (single letter code) |
|---|---|
| 75 | SCSDCLKSVDFIPSSLASS |
| 76 | SCAFDCPSSVARSPGEWSS |
| 77 | SCVDVMHADSPGPDGLNS |
| 78 | SCSSFEVSEMFTCAVSSYS |
| 79 | SCGLNFPLCSFVDFAQDAS |
| 80 | SCMLFSSVFDCGMLISDLS |
| 81 | SCVDYVMHADSPGPDGLNS |
| 82 | SCSENFMFNMYGTGVCTES |
| 83 | HKHPVTPRFFVVE |
| 84 | CNCYVTPNLLKHKCYKIC |
| 85 | CSHNHHKLTAKHQVAHKC |
| 86 | CDQNDIFYTSKKSHKSHC |
| 87 | SSDVYLVSHKHHLTRHNS |
| 88 | SDKCHKHWYCYESKYGGS |
| 89 | SDKSHKHWYSYESKYGGS |
| 90 | HHKLKHQMLHLNGG |
| 91 | GHHHKKDQLPQLGG |
| 92 | ssHKHPVTPRFFVVEsr |
| 93 | ssCNCYVTPNLLKHKCYKICsr |
| 94 | ssCSHNHHKLTAKHQVAHKCsr |
| 95 | ssCDQNDIFYTSKKSHKSHCsr |
| 96 | ssSSDVYLVSHKHHLTRHNSsr |
| 97 | ssSDKCHKHWYCYESKYGGSsr |
| 98 | HHKLKHQMLHLNGG |
| 99 | GHHHKKDQLPQLGG |
| Binding affinity for steel | |
| 100 | CFVLNCHLVLDRP |
| 101 | SCFGNFLSFGFNCEYALGS |
| 102 | DGFFILYKNPDVL |
| 103 | NHQNQTN |
| 104 | ATHMVGS |
| 105 | GINPNFI |
| 106 | TAISGHF |
| 107 | LYGTPEYAVQPLR |
| 108 | CFLTQDYCVLAGK |
| 109 | VLHDSYGPSVPL |
| 110 | VVDSTGYLRPVST |

TABLE 4-continued

Exemplary surface-binding peptides

| SEQ ID NO: | Amino acid sequence (single letter code) |
|---|---|
| 111 | VLQNATNVAPFVT |
| 112 | WWSSMPYVGDYTS |
| 113 | SSYFNLGLVKHNHVRHHDS |
| 114 | CHDHSNKYLKSWKHQQNC |
| 115 | SCKHDSEFIKKHVHAVKKC |
| 116 | SCHHLKHNTHKESKMHHEC |
| 117 | VNKMNRLWEPL |
| 118 | SSHRTNHKKNNPKKKNKTR |
| 119 | NHTISKNHKKKNKNSNKTR |

EXAMPLE 4

This example illustrates a method of making a peptide composition according to the presently disclosed subject matter, comprising coupling together at least one peptide having binding affinity for a surface material of a medical device (SBP) with at least one peptide having binding affinity for glycopeptide antibiotic (GABP). The peptide compositions according to the presently disclosed subject matter illustrated in this Example can be represented as comprising the following formula: SBP-L-GABP or GABP-L-SBP.

Using methods described herein and methods well known in the art for coupling (directly or via use of a linker) together two molecules, for example, a peptide having binding affinity for a surface material can be coupled to a peptide having binding affinity for glycopeptide antibiotic, in forming a peptide composition according to the presently disclosed subject matter useful for coating a surface material, such as that of a medical device. As apparent to one skilled in the art, a method of preference for coupling or linking two molecules will vary according to the reactive functionalities present on each molecule. As known to those skilled in the art, a reactive functionality which can be used in covalently coupling can comprise a chemical group selected from the group consisting of a maleimide, thiol, carboxy, hydrogen, phosphoryl, acyl, hydroxyl, acetyl, aldehyde, hydrophobic, amine, amido, dansyl, sulfhydryl, a succinimide (including but not limited to a succinimidyl ester or succinimidyl carbonate), a halogen, a thiol-reactive chemical group, an amine-reactive chemical group, a carboxyl-reactive chemical group, a hydroxyl-reactive chemical group, and a combination thereof.

In one illustration of this embodiment, a linker was used to couple a peptide having binding affinity for a surface material of a medical device with a peptide having binding affinity for glycopeptide antibiotic. Since many medical devices are comprised of a surface material comprising a metal, a peptide having binding affinity for metal was chosen as a representative surface-binding peptide for inclusion as a component in a composition according to the present subject matter. A peptide having an amino acid sequence consisting of SEQ ID NO:118, having binding affinity for a surface material comprising metal, was used as a representative peptide for inclusion as a component in a peptide composition according to the present subject matter. A peptide having amino acid sequences of SEQ ID NO: 1 was used as a representative peptide having binding affinity for glycopeptide antibiotic, and for inclusion as a component in a peptide composition according to the present subject matter. Using the following procedures, a linker was used to couple a peptide comprising an amino acid sequence of SEQ ID NO:1 to a peptide comprising an amino acid sequence of SEQ ID NO:118 to produce a peptide composition according to the presently disclosed subject matter comprising a surface-binding peptide coupled to a peptide having binding affinity for glycopeptide antibiotic (see, e.g., SEQ ID NO: 120).

The representative linker used was comprised of PEG (8-Amino-3,6-Dioxaoctanoic Acid) which is a hydrophilic bifunctional spacer with the shortest ether structure possible of PEG [poly(ethylene)glycol] with two ethylene oxide units. The linker is comprised of 2 PEG units; e.g., (HN—$CH_2$—$CH_2$—O—$CH_2$—$CH_2$—O—$CH_2$—C=O)$_2$ (termed hereinafter as a "(miniPEG)$_2$" linker). The composition according to the presently disclosed subject matter was synthesized such that the surface-binding peptide (comprising an amino acid sequence of SEQ ID NO: 118) is positioned at the C-terminus, the peptide having binding affinity for glycopeptide antibiotic (comprising an amino acid sequence of SEQ ID NO: 1) is positioned at the N-terminus, and in between and linking the 2 peptides is a miniPEG linker (see also, SEQ ID NO:120; SSSCLIDMYGVCHNFDGAYDSSRG-(miniPEG)$_2$-SSHRTNHKKNNPKKKNKTRGSSGK; the underlining signifies disulfide bond formation between the cysteine residues). The C-terminal amino acid of the composition was modified by amidation, while the N-terminal amino acid of the composition comprises a free amine.

The composition was synthesized in a linear manner using solid phase peptide synthesis on a fully automated peptide synthesizer. Standard Fmoc/t-Bu (fluoren-9-ylmethoxycarbonyl/tert-butyl) chemistry was employed using standard coupling reagents, methods, and resin. The Fmoc deprotection reactions were carried out using 20% piperidine in DMF (dimethyl formamide) for 15 minutes. The linear peptide cleavage from the resin was accomplished using Reagent K (TFA(trifluoroacetic acid): EDT (1,2-ethanedithiol):$H_2O$: phenol:thioanisole=82.5:2.5:5:5:5) at room temperature for 4 hours. The crude products were precipitated in cold ether. The pellet obtained after centrifugation was washed thrice with cold ether, and then lyophilized to give linear peptide as a white solid. The linear crude products were analyzed by analytical HPLC. Before subjecting it to cyclization reaction, the linear composition was purified by HPLC.

The cyclization reaction was performed to mediate intramolecular disulfide bond formation between the two cysteine residues in the amino acid sequence of the component of the composition comprising the peptide having binding affinity for glycopeptide antibiotic. The purified linear composition (~0.5 mg/ml) was dissolved in 10 mM phosphate buffer (pH 7.4), and then dimethyl sulfoxide (DMSO; 3-5%) was added dropwise with stirring to the solution containing the composition. The progress of the cyclization reaction was monitored by HPLC. After the disappearance of the starting linear composition (by HPLC), the reaction mixture was concentrated in vacuo and the crude cyclic product was subjected to semi-preparative RP (reverse phase)-HPLC purification. The crude cyclic composition was purified by HPLC, and the fractions containing the desired product were pooled and lyophilized to obtain a fluffy white powder comprising the composition containing the disulfide bonds. The final composition was further characterized by electrospray mass spectrometry. Using the synthesis procedure outlined above for a peptide composition comprising an amino acid sequence of SEQ ID NO:120, also synthesized was a composition comprising an amino acid sequence of SEQ ID NO:124: AUD-AUD-AUD-AUD-SSSCLIDMYGVCHNFDGAYDSSRG-(miniPEG)$_2$-SSHRTNHKKNNPKKKNKTRGSSGK) by adding 4 residues of aminoundecanoic acid ("AUD") sequentially, during linear synthesis, to the N-terminus.

In another embodiment, provided are peptides comprising amino acid sequence SEQ ID NO:125: (Myr-Ahx-SSCLID-IYGVCHNFDAY-(miniPEG)$_2$-HKKNNPKKKNK-TRGSSK), wherein "Myr" is myristic acid, and "Ahx" is aminohexanoic acid. Standard Fmoc/t-Bu chemistry using AA/TBTU/HOBt/NMM (1:1:1:2) as the coupling reagents was employed (AA is amino acid; TBTU is 0-(Benzotriazol-1-yl)-N,N,N',N'-tetramethyluronium tetrafluoroborate; HOBt is 1-Hydroxy-benzotriazole; NMM is N-methyl-morpholine). The base resin, Fmoc-PAL-Peg-PS (~0.20 mmol/g; [5-(4-Fmoc-aminomethyl-3,5-dimethoxyphenoxy)valeric acid]-polyethylene glycol-polystryrene resin) was used for peptide synthesis. Amino acids were used in 5 fold excess in the synthesis cycles, and all residues were doubly or triply coupled. The coupling reactions were monitored by Kaiser ninhydrin test or chloranil test. In order to suppress peptide aggregation, pseudoproline dipeptides Fmoc-SerSer(PsiMe, Me pro)-OH were employed and double coupled in 5 fold excess. Fmoc-Lys(Biotin)-OH and Fmoc-MiniPeg-$CO_2H$ were double coupled manually using the above coupling conditions. Fmoc deprotection reactions were carried out using 20% piperidine in DMF with 0.1 M HOBt. Aminohexanoic acid (Ahx) was introduced at the N-terminus of the resin-bound peptide followed by triple coupling of myristic acid using TBTU activation method. Peptide cleavage from the resin was accomplished using TFA cocktail (TFA: $H_2O$: TIS: Dodecanethiol=95:2:2:1) at room temperature for 4 hours or Reagent K (TFA: EDT:$H_2O$: phenol: thioanisole=82.5:2.5:5: 5:5) at room temperature for 3 hours.

The crude products were precipitated in cold ether. The pellet, obtained after centrifugation, was washed thrice with cold ether and then lyophilized to give white solid as crude peptide. The crude linear products were subjected to disulfide oxidation (cyclization) using 0.1 M iodine solution in methanol (final concentration ≤0.5 mg linear peptide/mL). The reaction mixture was stirred for 10 minutes to 1 hour at 25° C. After complete oxidation, as revealed by HPLC monitoring, the reaction was quenched with 5% sodium metabisulfite in water until a colorless solution was obtained. The reaction was lyophilized, and the crude cyclic composition was purified by HPLC using mobile eluants (A=$H_2O$/TFA (0.1% TFA) and B=acetonitrile/TFA (0.1% TFA). The fractions containing the desired product were pooled and lyophilized to obtain a fluffy white powder in >90% purity. The final product was further characterized by electrospray mass spectrometry.

In another embodiment, provided are peptides comprising amino acid sequence SEQ ID NO:126: (AUD-AUD-AUD-SSCLIDIYGVCHNFDAY-(miniPEG)$_2$-HKKNNP-KKKNKTRGSSK), and an amino acid sequence of SEQ ID NO:127 (AUD-AUD-AUD-AUD-SSCLIDIYGVCHNF-DAY-(miniPEG)$_2$-HKKNNPKKKNKTRGSSK). For synthesis of these compositions, Fmoc-AUD-$CO_2H$ was activated using 0.2 M HOBt solution in NMP (N-methylpyrrolidine), and manually coupled sequentially at the N-terminus of the peptide resin using TBTU/NMM method. Following each coupling, the Fmoc group was removed using 20% piperidine in DMF, and the resin subsequently coupled further with Fmoc-AUD-$CO_2H$ until completion of the reaction, as judged by ninhydrin test. The terminal Fmoc was removed before subjecting the peptide resin to full cleavage. The crude linear composition was cyclized using the iodine oxidation method and the crude cyclic composition was purified by RP-HPLC on a C-18 column. The final product was further characterized by electrospray mass spectrometry.

In another embodiment, provided are peptides comprising amino acid sequence SEQ ID NO:128: (SSCLIDIYGVCH-NFDAY-(miniPEG)$_2$-YFRAFRKFVKPFKRAFKGSSGK) and amino acid sequence SEQ ID NO:129: (Myr-Ahx-SS-CLIDIYGVCHNFDAY-(miniPEG)$_2$-YFRAFRKFVK-PFKRAFKGSSGK). Synthesis of these peptides was also accomplished by solid-phase synthesis on a Fmoc-PAL-PEG resin. Amino acids were used in 5× fold excess in the synthesis cycles and all residues were doubly or triply coupled. The coupling reactions were monitored by Kaiser ninhydrin test or chloranil test. Following completion of the synthesis, the terminal Fmoc group was removed and the crude product was cyclized to mediate intramolecular disulfide bond formation between the two cysteine residues. The purified linear composition (~0.5 mg/ml) was dissolved in 10 mM phosphate buffer (pH 7.4), and then dimethyl sulfoxide (DMSO; 3-5%) was added dropwise with stirring to the solution. The progress of the cyclization reaction was monitored by HPLC. After the disappearance of the starting linear peptide (HPLC), the reaction mixture was concentrated in vacuo and the crude cyclic product was subjected to semi-preparative RP-HPLC purification. The fractions containing the desired product were pooled and lyophilized to obtain a fluffy white powder. For the composition comprising an amino acid sequence of SEQ ID NO:129, myristic acid was introduced at the N-terminus of the synthesized product via a Ahx linker before subjecting it to iodine cyclization as described above. The crude cyclic product was subjected to RP-HPLC purification on a C-18 column. Each of the final products was further characterized by electrospray mass spectrometry.

In another embodiment, using the procedures described herein above for synthesis of SEQ ID NO: 120 and SEQ ID NO: 124, the following peptides SEQ ID NO: 130 & 131 were produced comprising a surface-binding peptide coupled to a peptide having binding affinity for glycopeptide antibiotic:

```
SEQ ID NO: 130:
SSCLIDIYGVCHNFDAY-(miniPEG)2-HKKNNPKKKNKTRGSSK

SEQ ID NO: 131:
SSCLIDIYGVCHNFDAY-(miniPEG)2-
SSHRTNHKKNNPKKKNKTRGSSGK.
```

EXAMPLE 5

Using the representative peptides made as described in Example 4, in this Example, the ability of the peptides to load and/or retain a glycopeptide antibiotic to a surface material was assessed. In this Example, a peptide composition according to the presently disclosed subject matter was applied to a metal bead (to represent a medical device surface) by contacting the peptide composition with the metal bead for a sufficient time for binding the peptide to the bead. The experimental results described below demonstrate that the peptide compositions can be used to bind and retain glycopeptide antibiotic to a surface material.

In one experiment, titanium beads were placed into wells of a 96 well plate. To each well was added a range of concentrations (1-50 μM) of peptide composition comprising at least one surface-binding peptide coupled to at least one glycopeptide antibiotic binding peptide and vancomycin at 200 μM. The appropriate negative controls were also included. The plate was incubated for 30 minutes, and then the wells and beads were washed 4 times with buffer. After washing, 10 mM HCl was added to each well to elute remaining vancomycin from the metal bead. Bound vancomycin was measured by HPLC assay at detection wavelength 214 nm. Experimental results are shown in Table 5. Each of the three peptide compositions tested displayed similar glycopeptide antibiotic loading results. In addition, binding assays performed using stainless steel rather than titanium beads as a representative surface material yielded similar results.

TABLE 5

Vancomycin loading on titanium surface by peptide compositions

| Peptide SEQ ID NO at 10 μM | Picomoles vancomycin/cm$^2$ |
|---|---|
| 120 | 61 |
| 130 | 83 |
| 131 | 76 |

The retention on a surface material of glycopeptide antibiotic by a composition of the presently disclosed subject matter over an extended period of time was also evaluated. In this experiment BODIPY-FL vancomycin and a binding assay using titanium beads were used to evaluate glycopeptide antibiotic retention by a peptide composition comprising SEQ ID NO: 120. BODIPY-FL vancomycin was added to the titanium bead and the relative amount of BODIPY-FL vancomycin immobilized to the bead was measured over a time period ranging from 45 minutes to 100 hours. The results of this assay indicate that in presence of the peptide composition, about 50% of the BODIPY-FL vancomycin remained on the metal surface after 3 hours; and detectable BODIPY-FL vancomycin remained on the bead surface for up to 100 hours.

EXAMPLE 6

The examples described herein previously demonstrate that a peptide composition according to the presently disclosed subject matter can be used to bind and retain glycopeptide antibiotic to a surface material. In this Example, the ability of the peptide compositions to inhibit bacterial growth on the surface material is demonstrated. To illustrate the antibacterial activity of the peptide compositions, an in vitro infection assay was performed. Briefly, a surface material was contacted with one of the peptide compositions such that the peptide binds to the surface material. The peptide composition can have glycopeptide antibiotic already bound thereto at the time of contacting the peptide with the surface material, or the glycopeptide antibiotic can be contacted with the peptide in a step subsequent to binding the peptide composition to the surface material. The surface material was washed to remove unbound glycopeptide antibiotic, and then contacted with bacterial cells (added from a culture in log phase growth) and incubated to promote bacterial growth. The surface material was washed, and any bacterial cells colonizing the surface material removed and plated to assess bacterial growth.

In one example, *Staphylococcus aureus* strain MZ100 was used as the representative bacterial cells. First, as a representative surface material, titanium beads were sterilized in acetone in a sonication bath, and then air dried in a sterile hood. The beads were individually placed in sterilized microfuge tubes (one bead per tube). Peptide composition SEQ ID NO: 119 (or buffer control) was added to the bead-containing tubes at a final concentration of 5 μM in sterile PBS. Vancomycin was added to the bead-containing tubes at a final concentration of 100 µM in sterile PBS. The tubes were incubated for 15 minutes at room temperature. To optimize uniform coating of the beads, each bead-containing tube was flipped to dislodge the bead after 5 and 10 minutes, respectively, and then the tube and contents were briefly vortexed. The beads were then washed two times with sterile PBS and then transferred to a sterile tube (one bead per tube) for culturing. To each culture tube was added 25 µl of a stock culture of strain MZ100 (~1×10$^5$ bacterial cells/ml; in early log phase growth). The tubes were then incubated at 37° C. After a 2 hour incubation, the culture tube contents were aspirated, and each bead was gently washed twice in the culture tube using sterile PBS (1 ml). To remove any bacteria colonized on the surface material, each bead was then sonicated in 1 ml sterile buffer using sonicator with a sterile microtip, and with care to prevent foaming or aerosols (e.g., output control at setting 4, duty cycle at 25%, for a total time period of about 1 minute). An equal aliquot from each tube was used to plate a tryptic soy broth agar plate, and the plates were then incubated at 37° C. overnight. The next day, the plates were examined for bacterial growth, and the number of bacterial colonies was quantified per plate. As shown in Table 6, bacterial growth on the plates was completely inhibited on the surface material treated with peptide composition SEQ ID NO: 119.

TABLE 6

Bacterial colony counts

| Treatment of surface material | # of bacterial colonies |
|---|---|
| Minus peptide composition | 4000 |
| Plus peptide composition | 0 |

In another demonstration of antibacterial activity and using similar methods as described for the titanium beads, titanium pins were used as the representative surface material, and vancomycin was used as a representative glycopeptide antibiotic. Acetone-sterilized titanium pins (1 mm diameter, 12 mm long) were first washed in PBS. These pins were then incubated in a solution (PBS) containing the respective composition (5 µM)+vancomycin (100 µM) for 15 minutes at room temperature, with intermittent inversion for coating. Each pin was then washed extensively in PBS and placed in 30 µL of S. aureus MZ100 cultured at 10$^6$ colony forming units (cfu) per mL, according to methods above. The coated pins were then inoculated in 30 mm lengths of 1.5 mm diameter silicone tubing, with closed ends. After incubation for two hours with shaking, the pin was placed in a new tube containing 1 mL PBS. After inverting several times, PBS was aspirated, and replaced with a fresh 1 mL of PBS. The pins were then sonicated at 20 kHz for four cycles of 15 seconds each. Supernatants (100 µL) and dilutions were plated on trypticase soy agar (TSA) plates, incubated for 24 hours at 37° C., and colonies were counted. An assay control included the same steps of the infection model, except that the pin is uncoated pin (i.e., without composition according to the presently disclosed subject matter bound thereto) ("Control"). As representative examples, compositions comprising the amino acid sequences of SEQ ID NOs: 125 and 126 were tested for antimicrobial activity using the in vitro infection model (see, Table 7, "A" & "B", respectively). As shown in Table 7, in this infection assay, the bacterial counts in the culture supernatants from the pins coated with a composition according to the presently disclosed subject matter were reduced by more than 10$^3$ colony forming units ("CFU") as compared to the Control.

TABLE 7

Bacterial colony counts

| Treatment of surface material | # of bacterial colonies (CFU) |
|---|---|
| Composition A | 100 |
| Composition B | <10 |
| Control | >100,000 |

From the results illustrated in Tables 6 & 7, it is clear that a composition according to the present subject matter, comprising glycopeptide antibiotic bound thereto, can be retained on surface material treated with the composition, and can inhibit bacterial growth on the treated surface material via the antibacterial activity of the glycopeptide antibiotic which is delivered to the surface material.

These results were further confirmed in an assay set up to visualize the antibacterial activity of the peptide composition of the presently disclosed subject matter on the surface material. Briefly, the surface material was treated either with glycopeptide antibiotic alone, the composition without glycopeptide antibiotic bound thereto, or the composition comprising glycopeptide antibiotic bound thereto, and then washed to remove unbound compound or composition. Added to each treated surface material was an inoculum of S. aureus strain MZ100. After an incubation period to promote bacterial growth on the surface material, the surface material was washed, and then bacterial growth was visualized by differential staining for live bacterial cells or dead bacterial cells retained on the surface material. The surface material treated with either glycopeptide antibiotic alone, or the composition without glycopeptide antibiotic bound thereto, showed live bacterial cells growing on the surface material. In contrast, dead bacterial cells were visualized on the surface material treated with composition comprising glycopeptide antibiotic bound thereto. These results suggest that the composition of the presently disclosed subject matter having glycopeptide antibiotic bound thereto demonstrates antibacterial activity on surface material coated with the composition.

In another experiment, antimicrobial activity of the peptide compositions was measured as follows. Titanium beads were placed into wells of a 96 well plate. To each well was added a 10 µM of peptide composition comprising at least one surface-binding peptide coupled to at least one glycopeptide antibiotic binding peptide and vancomycin at 200 µM. The appropriate negative controls were also included. The plate was incubated for 1 hour at 20° C., and then the wells and beads were washed 4 times with buffer. After washing, the beads were transferred to the well of a plate containing S. aureus in log phase growth and incubated at 37° C. for 18 hours. Bacterial growth was assessed by reading optical density at 600 nm. The experimental results showed complete inhibition of bacterial growth for the titanium beads loaded with each of the peptide SEQ ID NOs: 120, 130 & 131.

EXAMPLE 7

In this example, further illustrated are methods for applying a peptide composition according to the presently disclosed subject matter to a medical device. The methods comprise contacting the peptide composition with the surface of the medical device to which the composition is to be applied with an amount of the composition effective to deliver glycopeptide antibiotic in an amount effective for antibacterial activity. An effective amount of the peptide composition can be determined by a physician considering such factors that include, but are not limited to, the particular glycopeptide antibiotic to be delivered as part of the composition, the type of surface material to be treated, the site to which the medical device is to be positioned, and bacterial flora of the individual to be receiving the treated medical device. Using methods known in the art, an effective dosage can also be determined from results of pre-clinical and clinical studies using a composition according to the present subject matter. Progress or assessment of antibacterial activity localized by a composition according to the presently disclosed subject matter can be monitored by methods known in the art, such as by various imaging techniques (e.g., x-ray, computer-assisted tomography (CAT scan), magnetic resonance imaging (MRI), arthroscopy) for changes associated with infection, or culturing body fluid samples relevant to the positioning of a treated medical device.

The peptide composition can be applied to a medical device, wherein the composition comprises glycopeptide antibiotic already bound to the glycopeptide antibiotic binding domain at the time of application to the medical device. In another embodiment, the glycopeptide antibiotic is not yet bound at the time the peptide composition is applied to the medical device. With respect to the latter, in a further step of coating, the surface material having the peptide composition applied thereon is then contacted with a sufficient amount of glycopeptide antibiotic (in vitro or in vivo) under conditions suitable so that glycopeptide antibiotic binds to the peptide composition bound to the surface of the medical device. In one example, a peptide composition according to the presently disclosed subject matter is applied to the medical device before positioning the medical device in situ.

In another example, a peptide composition according to the presently disclosed subject matter is applied to a medical device in situ. For example, if the medical device is exposed through an open site in the body (e.g., such as in surgery), or is positioned at a site openly accessible outside the body (e.g., a dental implant accessible through an open mouth), a physician can spray or otherwise apply the peptide composition to the medical device in situ. In another example wherein the medical device is not readily accessible by applications such as a spray coating, a peptide composition according to the presently disclosed subject matter can be administered by injection at the site of the medical device such that the composition comes in contact with the medical device so as to bind to the medical device. To facilitate application of the peptide composition (e.g., by spray, soaking, or injection), the composition further comprises a pharmaceutically acceptable carrier. Conventional processes known in the art can be used to apply a peptide composition according to the presently disclosed subject matter to the one or more surfaces of a medical device to be coated. Depending on the nature of the medical device to which the peptide composition is to be applied, such processes are known to include, but are not limited to, soaking, mixing, dipping, brushing, spraying, and vapor deposition. For example, a solution or suspension comprising the peptide composition can be applied through the spray nozzle of a spraying device, creating droplets that coat the surface of the medical device to be coated. The coated medical device is allowed to dry. If desired, the coated medical device can be further processed prior to use (e.g., washed in a solution (e.g., water or isotonic buffer) to remove excess composition not specifically bound to the medical device; if for in vivo use, by sterilization using any one or methods known in the art for sterilizing polymer; etc.). Alternatively, the peptide composition and the medical device can each be separately sterilized prior to the process of combining them, and then performed under sterile conditions is the applying of the composition to one or more surfaces of the medical device.

In another process for applying the peptide composition to one or more surfaces of a medical device to be coated, a surface of the medical device to be coated is dipped into a liquid (e.g., solution or suspension, aqueous or solvent) containing the composition in an amount effective to coat the surface of the medical device. For example, the surface is dipped or immersed into a bath containing the peptide composition. Suitable conditions for applying the peptide composition as a coating composition include allowing the surface to be coated to remain in contact with the liquid containing the composition for a suitable period of time (e.g., ranging from about 5 minutes to about 5 hours; more preferably, ranging from 5 minutes to 60 minutes), at a suitable temperature (e.g., ranging from 10° C. to about 50° C.; more preferably, ranging from room temperature to 37° C.). If desired, the coated medical device can be further processed, as necessary for use (e.g., one or more of drying, washing, sterilization, and the like). These illustrative processes for applying a peptide composition to a medical device are not exclusive, as other coating and stabilization methods can be employed (as one of skill in the art will be able to select the methods used to fit the needs of the particular medical device and/or purpose).

Additionally, in a method according to the presently disclosed subject matter, a coating on a medical device surface comprising the peptide composition can be stabilized, for example, by air drying. However, these treatments are not exclusive, and other coating and stabilization methods can be employed. Suitable coating and stabilization methods are known in the art. For example, the surface of the medical device to be coated with the composition of the presently disclosed subject matter can be pre-treated prior to the coating step so as to enhance one or more of: the binding of the of the peptide composition to the surface; and the consistency and uniformity of the coating.

EXAMPLE 8

It is apparent to one skilled in the art, that based on the amino acid sequence of the glycopeptide antibiotic binding peptides, polynucleotides encoding such peptides can be synthesized or constructed, and such peptides can be produced by recombinant DNA technology as a means of manufacture (e.g., in culture) and/or in vivo production by introducing such polynucleotides in vivo. For example, it is apparent to one skilled in the art that more than one polynucleotide sequence can encode a peptide according to the present subject matter, and that such polynucleotides can be synthesized on the bases of triplet codons known to encode the amino acids of the peptide, third base degeneracy, and selection of triplet codon usage preferred by cell-free expression system or the host cell (typically a prokaryotic cell or eukaryotic cell (e.g., bacterial cells such as *E. coli*; yeast cells; mammalian cells; avian cells; amphibian cells; plant cells; fish cells; and insect cells; whether located in vitro or in vivo) in which expression is desired. It would be routine for one skilled in the art to generate the degenerate variants described above, for instance, to optimize codon expression for a particular host (e.g., change codons in the bacteria mRNA to those preferred by a mammalian, plant or other bacterial host such as *E. coli*).

For purposes of illustration only, and not limitation, provided are SEQ ID NOs:121-123, which are polynucleotides encoding amino acid sequences of SEQ ID NOs: 1, 2, and 3, respectively. In one illustrative embodiment, provided is a recombinant vector comprising a polynucleotide encoding a glycopeptide antibiotic binding domain peptide. The recombinant vector can be used for the recombinant production of a glycopeptide antibiotic binding peptide according to the presently disclosed subject matter. In one example, the polynucleotide can be added to a cell-free expression system known in the art for producing peptides or polypeptides. In another example, the polynucleotide can be positioned in an expression vector so that when the peptide is produced in host cells, it is produced as a fusion protein with other amino acid sequence (e.g., which assist in purification of the peptide; or as recombinantly coupled to a surface-binding domain), or as multiple copies or concatemers of the peptide. For example, there are sequences known to those skilled in the art which, as part of a fusion protein with a peptide desired to be expressed, facilitates production in inclusion bodies found in the cytoplasm of the prokaryotic cell used for expression and/or assists in purification of fusion proteins containing such sequence. Inclusion bodies can be separated from other prokaryotic cellular components by methods known in the art to include denaturing agents, and fractionation (e.g., centrifugation, column chromatography, and the like). In another example, commercially available vectors can be used into which can be inserted a desired nucleic acid sequence of interest to be expressed as a protein or peptide such that upon expression, purification of the gene product can be accomplished using methods standard in the art.

It is apparent to one skilled in the art that a nucleic acid sequence encoding a peptide having binding affinity for glycopeptide antibiotic according to the presently disclosed subject matter can be inserted into, and become part of a, nucleic acid molecule comprising a plasmid, or vectors other than plasmids; and other expression systems can be used including, but not limited to, bacteria transformed with a bacteriophage vector, or cosmid DNA; yeast containing yeast vectors; fungi containing fungal vectors; insect cell lines infected with virus (e.g. baculovirus); and mammalian cell lines having introduced therein (e.g., transfected or electroporated with) plasmid or viral expression vectors, or infected with recombinant virus (e.g. vaccinia virus, adenovirus, adeno-associated virus, retrovirus, etc.). Successful expression of the peptide requires that either the recombinant nucleic acid molecule comprising the encoding sequence of the peptide, or the vector itself, contain the necessary control elements for transcription and translation which is compatible with, and recognized by the particular host system used for expression.

Using methods known in the art of molecular biology, including methods described above, various promoters and enhancers can be incorporated into the vector or the recombinant nucleic acid molecule comprising the encoding sequence to increase the expression of the peptide, provided that the increased expression of the peptide is compatible with (for example, non-toxic to) the particular host cell system used. As apparent to one skilled in the art, the selection of the promoter will depend on the expression system used. Promoters vary in strength; i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, T7 promoter, recA promoter, ribosomal RNA promoter, the P.sub.R and P.sub.L promoters, lacUV5, ompF, bla, Ipp, and the like, can be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, herpes simplex virus promoter, and the CMV promoter.

In the case where expression of the peptide can be lethal or detrimental to the host cells, the host cell strain/line and expression vectors can be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside ("IPTG"); trp operon is induced when tryptophan is absent in the growth media; and tetracycline can be use in mammalian expression vectors having a tet sensitive promoter). Thus, expression of the peptide can be controlled by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

EXAMPLE 9

In this example, illustrated is a kit comprising a peptide composition according to the presently disclosed subject matter. The components of the kit can include a container containing a peptide composition comprising a peptide having binding affinity for glycopeptide antibiotic, and can further comprise one or more components selected from the group consisting of: at least one peptide having binding affinity for a surface material of a medical device coupled to the peptide having binding affinity for glycopeptide antibiotic, glycopeptide antibiotic bound to peptide having binding affinity for glycopeptide antibiotic, a pharmaceutically acceptable carrier, and a combination thereof. A preferred type of container is a vial, such as that typically used for solutions or lyophilized powders of medicaments, medicinals, drugs, coatings, and the like.

Alternatively, a component in the kit can be a first container comprising glycopeptide antibiotic, and a second container comprising a peptide composition according to the presently disclosed subject matter wherein glycopeptide antibiotic is absent. Thus, the contents of the first contrainer and second container can be mixed (e.g., the glycopeptide antibiotic can be added to the peptide composition) in a step of applying the composition to a surface material, rather than as part of a pre-formed composition containing glycopeptide antibiotic; or can be mixed with the peptide composition prior to applying the composition to a surface material. Other components of the kit can include, but are not limited to, a liquid for reconstitution (one or more containers containing a diluent or fluid which can be used to reconstitute a kit component, such as for reconstitution of a composition according to the presently disclosed subject matter and/or glycopeptide antibiotic that can be packaged in lyophilized or powder form); an applicator device for applying the peptide composition to a surface material (e.g., a soaking tray, brush, applicator pad, syringe, syringe needle, or combination thereof), instructions for use of the kit, a medical device to which is to be applied a composition according to the presently disclosed subject matter, and a combination thereof. A kit comprises such components packaged together, such as in a single sterile container (e.g., box, tray, pouch, or other form of conventional packaging). The kit can also comprise a plurality of individually packaged components, and the individual packages can then be contained within a single larger container. For use in the medical field or dental field, preferably the components will be sterilized within the package or container so that they are immediately ready for use in a sterile environment.

The foregoing description of the specific embodiments of the presently disclosed subject matter have been described in detail for purposes of illustration. In view of the descriptions and illustrations, others skilled in the art can, by applying, current knowledge, readily modify and/or adapt the presently disclosed subject matter for various applications without departing from the basic concept of the presently disclosed subject matter; and thus, such modifications and/or adaptations are intended to be within the meaning and scope of the appended claims.

What is claimed is:

1. A peptide composition comprising a glycopeptide antibiotic binding peptide from 17 to 100 amino acids in length, said peptide comprising: (i) a glycopeptide antibiotic binding domain having binding affinity for a glycopeptide antibiotic, said domain comprising an amino acid sequence of SEQ ID NO: 7, and (ii) a surface binding domain having affinity for a surface material of which a medical device is comprised, said surface binding domain comprising an amino acid sequence of any one of SEQ ID NOS: 14-119.

2. A method for coating a medical device, the method comprising applying a peptide composition of claim 1, wherein at least a portion of the peptide composition becomes bound to the surface material of which the medical device is comprised.

3. The method of claim 2, wherein the surface material of the medical device is selected from the group consisting of metal, nonmetal oxide, ceramic, polymer, and a combination thereof.

4. The method of claim 2, wherein the peptide composition further comprises a pharmaceutically acceptable carrier.

5. The peptide composition according to claim 1, wherein the glycopeptide antibiotic binding peptide has the formula:

GABP-L-SBP or SBP-L-GABP, wherein GABP refers to the glycopeptide antibiotic binding domain;

SBP refers to the surface binding peptide; and

L is a linker between SBP and GABP.

6. The peptide composition of claim 5, wherein the peptide composition comprising the formula GABP-L-SBP comprises SEQ ID NO: 131.

7. A method for coating a medical device, the method comprising applying the peptide composition of claim 5 wherein at least a portion of the peptide composition becomes bound to the surface of the medical device.

8. The method of claim 7, wherein the surface material of the medical device is selected from the group consisting of metal, nonmetal oxide, ceramic, polymer, and a combination thereof.

9. The method of claim 7, wherein the peptide composition further comprises a pharmaceutically acceptable carrier.

10. A medical device in which at least a portion of the surface of the medical device is coated with the peptide composition of claim 1, the medical device comprising one or more of hip endoprosthesis, artificial joints, jaw or facial implants, dental implants, tendon and ligament replacements, skin replacements, bone fixation implants, metal replacements and metal screws, prosthetic plates, metal nails or pinsor rivets, metal graft devices, or polymer-containing grafts.

11. A medical device in which at least a portion of the surface of the medical device is coated with the peptide composition of claim 5 the medical device comprising one or more of hip endoprosthesis, artificial joints, jaw or facial implants, dental implants, tendon and ligament replacements, skin replacements, bone fixation implants, metal replacements and metal screws, prosthetic plates, metal nails or pins or rivets, metal graft devices, or polymer-containing grafts.

12. A kit comprising a container containing a kit component, wherein the kit component comprises a peptide composition according to claim 1.

13. The kit according to claim 12, wherein packaged in a first container is the peptide having binding affinity for glycopeptide antibiotic, and packaged in a second container is a glycopeptide antibiotic.

14. The kit according to claim 12, wherein the kit comprises additional components selected from the group consisting of a liquid for reconstitution, an applicator device, instructions for use, a medical device to which the peptide composition is to be applied, and a combination thereof.

* * * * *

UNITED STATES PATENT AND TRADEMARK OFFICE
CERTIFICATE OF CORRECTION

PATENT NO. : 8,637,455 B2
APPLICATION NO. : 12/739353
DATED : January 28, 2014
INVENTOR(S) : Darby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this

Twenty-second Day of September, 2015

Michelle K. Lee
*Director of the United States Patent and Trademark Office*